United States Patent [19]
Henrie, II et al.

[11] Patent Number: 5,696,259
[45] Date of Patent: Dec. 9, 1997

[54] 2,4-DIAMINO-5-IODOPYRIMIDINES USEFUL AS PESTICIDE INTERMEDIATES

[75] Inventors: Robert N. Henrie, II, East Windsor; Clinton J. Peake, Trenton; Thomas G. Cullen, Milltown, all of N.J.; Walter H. Yeager, Yardley, Pa.; Mary E. Brown, Belle Mead; John W. Buser, North Brunswick, both of N.J.

[73] Assignee: FMC Corporation, Philadelphia, Pa.

[21] Appl. No.: 681,032

[22] Filed: Jul. 22, 1996

Related U.S. Application Data

[60] Division of Ser. No. 398,205, Mar. 2, 1995, Pat. No. 5,662,294, which is a continuation-in-part of Ser. No. 241,083, May 11, 1994, abandoned.

[51] Int. Cl.[6] .............. C07D 239/48; C07D 401/04; C07D 413/04
[52] U.S. Cl. .............. 544/82; 544/323; 544/122
[58] Field of Search ................. 544/323, 122, 544/82

[56] References Cited

FOREIGN PATENT DOCUMENTS

| 2256289 | 6/1974 | Germany | .......... C07D 51/42 |
|---|---|---|---|
| 3445293 | 6/1986 | Germany | .......... C07D 239/48 |
| 3717480 | 1/1988 | Germany | .......... C07D 239/48 |

OTHER PUBLICATIONS

Chemical Abs. 105: 115090 h.
Chemical Abs. 81: 63670 m.
Scwamborn et al., (CA 105:115090h, DE 3,445,293; Jun. 12, 1984).

*Primary Examiner*—Mukund J. Shah
*Assistant Examiner*—Sabiha Qazi
*Attorney, Agent, or Firm*—Stanford M. Back; Robert M. Kennedy

[57] ABSTRACT

This invention describes 2,4-diamino-5-iodopyrimidines II where R, R1, R2, and R3 are independently selected from hydrogen, alkyl, cycloalkyl, alkoxyalkyl, alkoxyalkoxyalkyl, and arylalkyl; or, R1 and R2, and R3 and R, each independently, when taken together with pentylene or 3-oxapentylene, form piperidine and morpholine ring systems respectively; and R4 is hydrogen or lower alkyl. These compounds are useful intermediates in the preparation of insecticides I where U is an optionally substituted alkenylene.

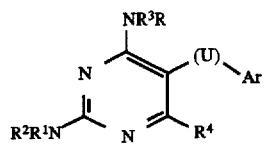

I

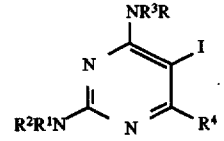

II

1 Claim, No Drawings

2,4-DIAMINO-5-IODOPYRIMIDINES USEFUL AS PESTICIDE INTERMEDIATES

CROSS REFERENCE TO RELATED APPLICATION

This application is a division of application Ser. No. 08/398,205, filed Mar. 2, 1995 now U.S. Pat. No. 5,662,294, which is a continuation-in-part of Ser. No. 08/241,083 filed May 11, 1994 in the names of Hende et al. is now abandoned.

BACKGROUND OF THE INVENTION

This invention relates to 5-substituted-2,4-diaminopyrimidine compounds (hereinafter "2,4-diaminopyrimidines") and compositions containing the same which are useful for controlling agricultural pests such as insects and acarids. Still more particularly, this invention relates to certain 2,4-diaminopyrimidine compounds and compositions, and their use as acaricides, particularly of the order Lepidoptera such as the tobacco budworm, and Coleoptera, such as the Mexican bean beetle.

SUMMARY OF THE INVENTION

In accordance with the present invention it has been found that novel substituted-2,4-diaminopyrimidines, and agriculturally acceptable salts thereof, when present in insecticidally or acaricidaily effective amounts, and with a suitable agricultural carrier, are useful as active ingredients in the insecticidal compositions and methods of this invention. These novel pyrimidines may be represented by the following structure:

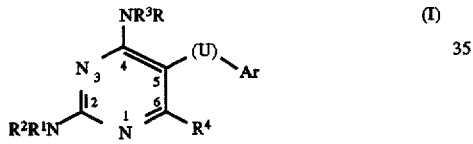
(I)

wherein

R, $R^1$, $R^2$, and $R^3$ are independently selected from hydrogen, alkyl [e.g., —$CH_3$, —$C_2H_5$, —$C_3H_7$, —$C(CH_3)_3$, —$CH(CH_3)_2$, n-$C_8H_{17}$], cycloalkyl (e.g., cyclohexyl), alkoxyalkyl (e.g., —$C_3H_6OC_2H_5$), alkoxyalkoxyalkyl (e.g., —$C_2H_4OC_2H_4OC_2H_5$), arylalkyl (e.g., phenylmethyl or 2-pyridylmethyl), alkylcarbonyl, [e.g., —(C=O)$CH_3$, —(C=O)CH($CH_3$)$_2$, —(C=O)$C_{11}H_{23}$], cycloalkylcarbonyl (e.g., cyclohexylcarbonyl), alkoxycarbonyl [e.g., —(C=O) $OC_2H_5$], alkoxyalkylcarbonyl [e.g., —(C=O) $C_2H_4OC_2H_5$], alkoxyalkoxyalkylcarbonyl [e.g., —(C=O)$C_2H_4OC_2H_4OC_2H_5$], arylcarbonyl (e.g., benzoyl), pyridinylcarbonyl (e.g., 3-pyridinylcarbonyl), aryloxyalkyl [e.g., —C(=O) $CH_2OC_6H_5$], haloalkylcarbonyl [e.g.,—C(=O) ($CH_2$)$_2$F], and cyanoalkylcarbonyl [e.g.,—C(=O) ($CH_2$)$_3$CN];

wherein R, $R^1$, $R^2$, and $R^3$ contain up to about 12 carbon atoms, and wherein the alkyl groups may be straight or branched chain; or $R^1$ and $R^2$, and $R^3$ and R, each independently, when taken together with pentylene or 3-oxapentylene, form piperidine and morpholine ring systems respectively;

$R^4$ is hydrogen or lower alkyl [e.g., —$CH_3$, —$C_2H_5$, —$CH(CH_3)_2$];

U is a $C_3$ to about $C_{12}$, preferably $C_{3-8}$, alkenylene [e.g., —CH=CHCH$_2$—, —CH=CHCH($CH_3$)—, —CH=CHC($CH_3$)$_2$—], haloalkenylene [e.g., —CH=CHCF$_2$—, —CF=CHC($CH_3$)$_2$—], alkoxyalkenylene [e.g., —CH=CHCH(O$CH_3$)—], 2-(1-substituted-1-cycloalkyl)alkenylene [e.g., 2-[1-substituted-1-cyclopentyl]ethenylene], 2-(substituted-oxacycloalkyl)alkenylene [e.g., 2-(4-substituted-4-tetrahydropyranyl)ethenylene], 2-[2-substituted-2-(1,3-dioxacycloalkyl)]alkenylene [e.g., 2-[2-substituted-2-(1,3-dioxolanyl)]ethenylene, or 2-[2-substituted-2-(1,3-dioxanyl)]ethenylene], dialkylsilylalkenylene [e.g., —CH=CHSi($CH_3$)$_2$—], oxoalkenylene (e.g., 3-oxo-1-propenylene), or hydroxyalkenylene [e.g., —CH=CHC(OH)$CH_3$—]; or a $C_3$ to about $C_{12}$, preferably $C_{3-8}$, alkynylene [e.g., —C≡CCH$_2$—, —C≡CCH($CH_3$)—, —C≡CC ($CH_3$)$_2$—]; alkoxyalkynylene [e.g., —C≡CCH (O$CH_3$)—], heterocycloalkylalkynylene [e.g., 3-(1-piperidinyl)-1-propynylene], 2-(1-substituted-1-cycloalkyl)alkynylene [e.g., 2-[1-substituted-1-cyclopentyl]ethynylene], 2-(substituted-oxacycloalkyl) alkynylene [e.g., 2-(4-substituted-4-tetrahydropyranyl) ethynylene], 2-[2-substituted-2-(1,3-dioxacycloalkyl)] alkynylene [e.g., 2-[2-substituted-2-(1,3-dioxolanyl)] ethynylene, or 2-[2-substituted-2-(1,3-dioxanyl)] ethynylene], dialkylsilylalkynylene [e.g., —C≡CSi ($CH_3$)$_2$—], oxoalkynylene (e.g., 3-oxo-1-propynylene), or hydroxyalkynylene [e.g., —C≡C (OH)$CH_3$—];

Ar is

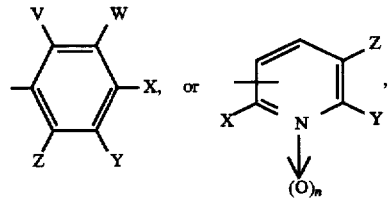

wherein

V, W, X, Y, and Z are independently selected from hydrogen, halogen (e.g., chloro), lower alkyl (e.g., —$CH_3$ or —C($CH_3$)$_3$), lower haloalkyl (e.g., —$CF_3$), lower alkoxy (e.g., —$OC_4H_9$ or —O$CH_3$), lower haloalkoxy (e.g., —$OCF_3$), lower alkoxyalkyl (e.g., —$CH_2OCH_3$), lower alkylsulfonyl (e.g., —$SO_2CH_3$), substituted aryl (e.g., 4-fluorophenyl), substituted aryloxy (e.g., 4-chlorophenoxy), and hydroxy; and n is 0 or 1;

and agriculturally acceptable salts thereof, including hydrochloric acid salt, ethanesulfonic acid salt, gluconic acid salt, and pamoic acid salt.

Of the compounds of the present invention, among the more preferred ones, particularly as insecticides and acaricides, are those wherein R, $R^1$, $R^2$, and $R^3$ are independently selected from hydrogen, lower alkyl (e.g., —$CH_3$, —$C_2H_5$, —$C_3H_7$), alkoxyalkoxyalkyl (e.g., —$C_2H_4OC_2H_4OC_2H_5$), alkylcarbonyl [e.g., —(C=O)$CH_3$, —(C=O)CH($CH_3$)$_2$], alkoxycarbonyl [e.g., —(C=O)O$C_2H_5$], alkoxyalkylcarbonyl [e.g., —C(=O)$CH_2OC_2H_5$, —C(=O)($CH_2$) $_3OC_2H_5$, —C(=O)$C_2H_4OC_2H_5$], alkoxyalkoxyalkylcarbonyl [e.g., —(C=O)$C_2H_4OC_2H_4OC_2H_5$], pyridinylcarbonyl (e.g., 3-pyridinylcarbonyl), and haloalkylcarbonyl [e.g., —C(=O)($CH_2$)$_2$F];

$R^4$ is lower alkyl [e.g., —$CH_3$];

U is a $C_{3-8}$ alkenylene [e.g., —CH=CHCH($CH_3$)—, —CH=CHC($CH_3$)$_2$—], 2-(1-substitute-1-cycloalkyl)

alkenylene [e.g., 2-[1-substituted-1-cyclopentyl] ethenylene], 2-(substituted-oxacycloalkyl)alkenylene [e.g., 2-(4-substituted-4-tetrahydropyranyl) ethenylene], 2-[2-substituted-2-(1,3-dioxacycloalkyl) alkenylene [e.g., 2-[2-substituted-2-(1,3-dioxolanyl)] ethenylene, 2-[2-substituted-2-(1,3-dioxanyl)] ethenylene], or dialkylsilylalkenylene [e.g., —CH=CHSi(CH$_3$)$_2$—]; or a C$_{3-8}$ alkynylene [e.g., —C≡CCH(CH$_3$)—, —C≡CC (CH$_3$)$_2$—], 2-(1-substituted-1-cycloalkyl)alkynylene [e.g., 2-[1-substituted-1-cyclopentyl]ethynylene], 2-(substituted-oxacycloalkyl)alkynylene [e.g., 2-(4-substituted-4-tetrahydropyranyl)ethynylene], 2-[2-substituted-2-(1,3-dioxacycloalkyl)]alkynylene [e.g., 2-[2-substituted-2-(1,3-dioxolanyl)]ethynylene, 2-[2-substituted-2-(1,3-dioxanyl)]ethynylene], or dialkylsilylalkynylene [e.g., —C≡CSi(CH$_3$)$_2$—]; and Ar is as defined above in Formula (I), wherein W, X, and Y are independently selected from hydrogen, halogen (e.g., chloro, or fluoro), haloalkyl (e.g., —CF$_3$), lower alkyl (e.g., —C(CH$_3$)$_3$), lower alkoxy (e.g., —OCH$_3$), and lower alkylsulfonyl (e.g., —SO$_2$CH$_3$);

V, and Z are hydrogen; and n is 0 or 1.

Of these compounds, those which are particularly preferred are those having an unsaturated bridge at the pyrimidine 5-position wherein the unsaturation is adjacent to the pyrimidine.

The above preferred 2,4-diaminopyrimidine compounds falling within the scope of Formula (I) are preferred because of their high pesticidal activity, and may be used in controlling pests by applying to the locus where control is desired an insecticidal or acaricidal amount of these compounds admixed in a suitable agricultural carrier. When thus applied to infected crops such as cotton, vegetables, fruits or other crops, these compounds are highly effective against an array of pests, particularly those shown in the tables below.

For the purposes of this invention, as regards the above substituent groups, the following definitions apply:

The term alkyl, alone or as part of a larger moiety, as used herein, generally, except where indicated, includes straight or branched chained alkyl groups of up to about 14 carbon atoms, desirably up to about 12 carbon atoms, and preferably lower straight or branched alkyl of up to about 6 carbon atoms; while halogen includes chlorine, bromine, fluorine and iodine atoms. The terms haloalkyl and haloalkoxy include straight or branched chain alkyl of 1 to 14 carbon atoms, preferably lower straight or branched alkyl of 1 to 6 carbon atoms, wherein one or more hydrogen atoms have been replaced with halogen atoms, as, for example, trifluoromethyl and 2,2,2-trifluoroethoxy, respectively. The terms lower alkoxy includes those moieties having 1 to 6 carbon atoms, e.g., ethoxy, etc.

In R, R$^1$, R$^2$, and R$^3$, the carbon atom content of these moieties, including the carbon atoms of the alkyl groups, preferably lower alkyl, which may be straight or branched chain, and which am part of these moieties, is desirably from 1 up to about 12 carbon atoms. Thus, for example R, R$^1$, R$^2$, and R$^3$ include C$_{1-12}$ alkyl; C$_{2-12}$ alkylcarbonyl, haloalkylcarbonyl, alkoxyalkyl and alkoxycarbonyl; C$_{3-12}$ cycloalkyl, alkoxyalkoxyalkyl, alkoxyalkylcarbonyl, and cyanoalkylcarbonyl; C$_{4-12}$ cycloalkylcarbonyl and alkoxyalkoxyalkylcarbonyl; and C$_{7-12}$ arylalkyl, aryloxyalkyl and arylcarbonyl, in which lower alkyl is preferably C$_1$ to about C$_6$.

The terms aryl and substituted aryl include optionally substituted phenyl, and naphthyl, preferably phenyl or substituted phenyl; the terms arylcarbonyl and substituted arylcarbonyl include benzoyl and naphthoyl, preferably benzoyl or substituted benzoyl; while the terms aryloxy and substituted aryloxy include phenoxy and naphthoxy.

The term "substituted" as applied to the V, W, X, Y, and Z groups of the substituted aryl moiety in Formula (I) above, includes such substituents as lower alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl, wherein lower alkyl is preferably C$_1$ to about C$_6$.

In the definition of the U-moiety, the carbon atom limitation of C$_3$ to about C$_{12}$, and preferably C$_{3-8}$, will be understood to apply to all of the recited unsaturated groups; while the term heterocyclo, as applied to the heterocycloalkylalkynylene moiety of the above described U group, includes 1-piperidinyl, 1-morpholinyl, and 1-pyrrolidinyl.

It will be understood from the structure of Formula (I), above, that the term "substituted" as employed in the definition of the U-moiety is for the sole purpose of designating the point of attachment of the aryl group, Ar, to the U-moiety, as shown by that structure.

DETAILED DESCRIPTION OF THE INVENTION

Synthesis of The Compounds

The compounds of the present invention may readily be prepared by methods known to one skilled in the art. Briefly, for those compounds wherein the U moiety of Formula (I) is straight or branched chain alkenylene [e.g., —CH=CHCH(CH$_3$)—, —CH$_2$CH=C(CH$_3$)—], an appropriately substituted phenylmagnesium bromide may be reacted with an oxoalkanenitrile, for example, 5-oxohexanenitrile, affording the corresponding (substituted phenyl)hydroxyalkanenitrile. The so-prepared (substituted phenyl)-hydroxyalkanenitrile can in turn be dehydrated using p-toluenesulfonic acid in toluene, yielding a corresponding mixture of alkenenitrile isomers, for example, 5-(substituted phenyl)-4-hexenenitrile and 5-(substituted phenyl)-5-hexenenitrile. The alkenenitrile mixture may then be treated with n-butyllithium, and acylated with ethyl acetate, affording the corresponding mixture of oxoalkenes, for example, 3-cyano-2-oxo-6-(substituted phenyl)-5-heptene and 3-cyano-2-oxo-6-(substituted phenyl)-6-heptene. The oxoalkene mixture may in turn be reacted with an alcohol in the presence of p-toluenesulfonic acid, yielding the corresponding dienol ether mixture, for example, 3-cyano-2-pentoxy-6-(substituted phenyl)-2,5-heptadiene and 3-cyano-2-pentoxy-6-(substituted phenyl)-2,6-heptadiene. In the final step of this preparation, the diene mixture can be cyclized with guanidine hydrochloride under basic conditions, yielding a mixture of targeted 2,4-diaminopyrimidine compounds, for example, trans-2,4-diamino-6-methyl-5-[3-(4-chlorophenyl)-1-butenyl] pyrimidine (Compound 7 of Table I below) and trans-2,4-diamino-6-methyl-5-[3-(4-chlorophenyl)-2-butenyl] pyrimidine (Compound 34). The targeted isomers are separated by column chromatography. Example 1 provides a detailed description of how this reaction is conducted.

In the procedure described above, guanidine hydrochloride may be replaced with a substituted guanidine, for example, 1-ethylguanidine hydrochloride, which yields 2-(substituted amino)-4-amino-6-methyl-5-substituted pyrimidines, for example, 2-ethylamino-4-amino-6-methyl-5-[3-(4-chlorophenyl)-1-butenyl]pyrimidine (Compound 47) and 2-ethylamino-4-amino-6-methyl-5-[3-(4-chlorophenyl)-2-butenyl]pyrimidine. Example 7 provides a detailed description of how this reaction is conducted.

In another route, wherein U is straight or branched chain alkenylene [e.g., —$CH_2C$=$C(CH_3)$—], an appropriately substituted acetophenone, when treated with vinylmagnesium bromide, yields the corresponding 3-hydroxy-3-(substituted phenyl)-1-butene. Treatment of the 1-butene derivative with pyridine and thionyl chloride effects migration of the double bond and chlorination, yielding the corresponding chlorinated 2-butene derivative, for example, 1-chloro-3-(substituted phenyl)-2-butene. The chloro-2-butene derivative is then treated with sodium hydride and reacted with ethyl acetoacetate, affording the appropriate ethyl hexenoate, for example, ethyl 2-methylcarbonyl-5-(substituted phenyl)-4-hexenoate. The so-prepared ethyl hexenoate may in turn be cyclized with guanidine hydrochloride, affording the corresponding 2-amino-4-hydroxy-6-methylpyrimidine, for example, 2-amino-4-hydroxy-6-methyl-5-[3-(substituted phenyl)-2-butenyl] pyrimidine. The pyrimidine intermediate is then chlorinated with phosphorous oxychloride and phosphorous pentachloride, and further cyclized with sodium azide and ammonium chloride, affording the corresponding 5-amino-7-methyltetrazolo[1,5-c]pyrimidine, for example, 5-amino-7-methyl-8-[3-(substituted phenyl)-2-butenyl]tetrazolo[1,5-c]pyrimidine. The tetrazolo[1,5-c]pyrimidine ring is then opened with activated zinc and acetic acid, affording the targeted 2,4-diamino-6-methylpyrimidine, for example, 2,4-diamino-6-methyl-5-[3-(substituted phenyl)-2-butenyl]pyrimidine. Example 2 provides a detailed description of how this reaction is conducted.

In addition to the routes described above, those compounds wherein U is straight or branched chain alkynylene [e.g., —C≡—$CCH_2$—, —C≡$CCH(CH_3)$—, —C≡CC$(CH_3)_2$—], oxoalkynylene (e.g., 3-oxo-1-propynylene), or dialkylsilylalkynylene [e.g., —C≡$CSi(CH_3)_2$—], may be prepared by the Heck coupling of 2,4-diamino-5-iodo-6-methylpyrimidine with the appropriately substituted terminal alkyne, oxoalkyne or dialkylsilylalkynylene in the presence of bis(triphenylphosphine)palladium(II) chloride and copper iodide in triethylamine. Targeted compounds prepared using the Heck coupling include, for example, 2,4-diamino-6-methyl-5-(3-phenyl-1-propynyl)pyrimidine (Compound 39), 2,4-diamino-6-methyl-5-[3-(4-chlorophenyl)-3-oxo-1-propynyl]pyrimidine (Compound 46), and 2,4-diamino-6-methyl-5-[(4-chlorophenyl) dimethylsilylethynyl]pyrimidine (Compound 45). Examples 3, 9, 10, and 15 provide detailed descriptions of how these reactions are conducted.

Other compounds wherein U is straight or branched chain alkenylene [e.g., —CH=$CHCH_2$—, —CH=CHC$(CH_3)_2$—, —CH=$CHC(CH_3)_2CH_2$—, —CH=CHCH$(OCH_3)$—], haloalkenylene (e.g., —CH=$CHCF_2$—, —CF=$CHC(CH_3)_2$—), oxoalkenylene (e.g., 3-oxo-1-propenylene), 2-(1-substituted-1-cycloalkyl)alkenylene [e.g., 2-[1-substituted-1-cyclopentyl]ethylene], and dialkylsilylalkenylene [e.g., —CH=$CHSi(CH_3)_2$—] maybe prepared by the Stille coupling of 2,4-diamino-5-iodo-6-methylpyrimidine with the appropriately substituted alkenyl, haloalkenyl, or oxoalkenyl trialkyl tin derivatives. Targeted compounds prepared using the Stille coupling include, for example, 2,4-diamino-6-methyl-5-[3,3-difluoro-3-(4-chlorophenyl)-1-propenyl]pyrimidine (Compound 4), 2,4-diamino-6-methyl-5-[3-(4-chlorophenyl)-3-oxo-1-propenyl]pyrimidine (Compound 27), 2,4-diamino-6-methyl-5-[3-(4-chlorophenyl)-3-methyl-1-butenyl]pyrimidine (Compound 21 ), 2,4-diamino-6-methyl-5-[2-[1-(4-chlorophenyl)-1-cyclopentyl]ethenyl] pyrimidine (Compound 24), and 2,4-diamino-6-methyl-5-[1-fluoro-3-methyl-3-(4-chlorophenyl)-1-butenyl] pyrimidine (Compound 62). Examples 4, 5, 6 11, 13, 14 and 16 provide detailed descriptions of how these reactions are conducted.

Optionally, compounds prepared as described above may be further reacted to obtain other compounds included within the scope of the present invention. For example, a 2,4-diaminopyrimidine or a 2-(mono-substituted)amino-4-aminopyrimidine may be reacted with an acid anhydride, such as acetic anhydride or isobutyric anhydride, in the presence of 4-dimethylaminopyridine, affording the corresponding 2,4-di(substituted)aminopyrimidines. Two compounds, trans-2,4-di-(1-methylethylcarbonylamino)-6-methyl-5-[3-(4-chlorophenyl)-1-butenyl]pyrimidine (Compound 54), and 2-[(ethyl)(methyl-carbonyl)]amino-4-methylcarbonylamino-6-methyl-5-[3-(4-chlorophenyl)-1-butenyl]pyrimidine (Compound 58) are compounds prepared in this manner. Examples 8 and 12 provide detailed descriptions of how these reactions are conducted.

Selected compounds prepared as described above may also be further reacted to obtain other compounds included within the scope of the present invention. These reactions include treating a carbonyl-containing compound, for example 2,4-diamino-6-methyl-5-[3-(4-chlorophenyl)-3-oxo-1-propynyl]pyrimidine (Compound 46) with, for example, ethylene glycol in the presence of a catalyst, affording the corresponding ketal, for example, 2,4-diamino-6-methyl-5-[2-[2-(4-chlorophenyl)-2-(1,3-dioxolanyl)] ethynyl]pyrimidine (Compound 108). Example 16 provides a detailed description of how this reaction may be conducted.

Example 17, wherein U is alkenylene [e.g., —CH=CHC$(CH_3)_2$—], teaches a desirable method for preparing Compound 68, in which a substituted phenylmethyl halide, for example, 4-trifluoromethylphenylmethyl bromide, is treated with potassium cyanide in water, yielding the corresponding substutited phenylacetonitrile. The so-prepared acetonitrile may then be treated with potassium tert.-butoxide in tetrahydrofuran, then reacted with a lower alkyl halide, for example iodomethane, yielding the corresponding 2-alkyl-2-(substituted phenyl)propanenitrile. The propanenitrile is then treated with diisobutylaluminium hydride which converts it to the corresponding propanaldehyde, for example, 2-methyl-2-(4-trifluoromethylphenyl)propanaldehyde. The propanaldehyde may then be reacted with bromomethyl triphenylphosphonium bromide and potassium tert.-butoxide in tetrahydrofuran, affording the cis/trans-1-bromo-3-alkyl-3-(substituted phenyl)-1-butene intermediate. This compound, in turn can be dehydrohalogenated with potassium tert.-butoxide in tert.-butanol, affording the corresponding butyne, for example, 3-methyl-3-(4-trifluoromethylphenyl)-1-butyne. Using methods taught by G. W. Kabaika et al. [Synthetic Communications, 11(3), 247–251 (1981) and Synthetic Communications, 13(12), 1027–1032 (1983)], the 1-butyne is reacted with 1,3,2-benzodioxaborole to form a boronic acid, in the present case, trans-3-methyl-3-(4-trifluoromethylphenyl)-1-butenylboronic acid. The sodium salt of the boronic acid may in turn be reacted with 2,4-diamino-5-iodo-6-methylpyrimidine in the presence of tetrakistriphenylphosphine palladium(0) in ethanol, yielding the targeted trans-2,4-diamino-6-methyl-5-[3-(4-trifluoromethylphenyl)-3-methyl-1-butenyl]pyrimidine (Compound 68).

Compound 84, exemplified in Example 18, may be prepared by methods taught above.

In Example 19, the commercially available 2-amino-4-chloro-6-methylpyrimidine when reacted with an appropriate lower alkylamine, for example, propylamine in ethanol, yields 2-amino-4-alkylamino-6-methylpyrimidine. The 4-alkylaminopyrimidine may then be halogenated with iodine monochloride to give the corresponding 2-amino-4-alkyiamino-5-iodo-6-methylpyrimidine, which is in turn reacted with an appropriate boronic acid, as described in Example 17, yielding, for example, the targeted trans-2-amino-4-propylamino-6-methyl-5-[3-(4-trifluoromethylphenyl)-3-methyl-1-butenyl]pyrimidine (Compound 140).

In Example 20, using a method analogous to Example 8, above, a targeted 2,4-diaminopyrimidine, for example, trans-2-amino-4-propylamino-6-methyl-5-[3-(4-trifluoromethylphenyl)-3-methyl-1-butenyl]pyrimidine may be reacted with an add anhydride, such as acetic anhydride or isobutyric anhydride, in the presence of 4-dimethylaminopyridine, affording the corresponding 2,4-di(substituted)aminopyrimidine, for example, trans-2-(1-methylethylcarbonyl)amino-4-[(propyl)(1-methylethylcarbonyl)amino]-6-methyl-5-[3-(4-trifluoromethylphenyl)-1-butenyl]pyrimidine (Compound 143).

In Examples 21 and 22, employing methods analogous to those of Example 17 and 18, there may be obtained the corresponding 3-(2,6-di-t-butyl-4-pyridyl)-1-butenyl or -1-butynyl compound by using, e.g., 4-bromomethyl-2,6-di-t-butylpyridine (which may be prepared by the method of C. J. Hou et al, JOC 47 (1982), pp. 1977–9) in place of the 4-trifluoromethylphenyl starting compound of Example 17. Desirably, the acidification step of Example 17, Step C, may be replaced with sodium fluoride treatment as taught by L. E. Overman et al, Tetrahedron Letters, 25 (1984), pp. 5737–5738. Further, in the preparation of the butyne derivative of Example 18, the butyne product analogous to that of Example 17, Step F may be used as an intermediate starting material.

EXAMPLES

The following examples, which disclose the preparation of representative compounds of this invention (see Table 1), are for the purpose of illustrating methods for the preparation of the compounds employed in the methods and formulations of this invention.

Example 1

SYNTHESIS OF trans-2,4-DIAMINO-6-METHYL-5-[3-(4—CHLOROPHENYL)-1-BUTENYL] PYRIMIDINE (COMPOUND 7)

AND trans-2,4-DIAMINO-6-METHYL-5-[3-(4—CHLOROPHENYL)-2-BUTENYL]PYRIMIDINE (COMPOUND 34)

Step A Synthesis of 5-hydroxy-5-(4-chlorophenyl) hexanenitrile as an intermediate One hundred mL (0.1 mole) of a 1.0 molar solution of 4-chlorophenylmagnesium bromide in diethyl ether is stirred, and a solution of 11.4 mL (0.1 mole) of 5-oxohexanenitrile in 125 mL of diethyl ether is added dropwise. The exothermic reaction causes the reaction mixture temperature to rise to about 31° C. The reaction mixture is then cooled in an ice-bath, and the dropwise addition of the nitrile solution is continued. The complete addition requires about 30 minutes. Upon completion of addition, the reaction mixture is allowed to warm to ambient temperature where it is stirred for two hours. The reaction mixture is then poured into 500 mL of water and made acidic with aqueous 2N hydrochloric acid. The organic layer is separated, and the aqueous layer is extracted with one 250 mL portion of diethyl ether. The organic layers are combined and dried with magnesium sulfate. The mixture is filtered, and the filtrate is concentrated under reduced pressure to a residual oil. The oil is subjected to column chromatography on silica gel, using methylene chloride as the eluant. The product-containing fractions are combined and concentrated under reduced pressure, yielding 15.0 grams of 5-hydroxy-5-(4-chlorophenyl)hexanenitrile. The NMR spectrum is consistent with the proposed structure.

Step B Synthesis of a mixture of 5-(4-chlorophenyl)-4-hexenenitrile and 5-(4-chlorophenyl)-5-hexenenitrile as intermediates In a reaction vessel fitted with a Dean-Stark trap to collect the water by-product, and under a nitrogen atmosphere, a stirred solution of 15.0 grams (0.067 mole) of 5-hydroxy-5-(4-chlorophenyl)hexanenitrile and 0.5 gram (catalyst) of p-toluenesulfonic acid in 200 mL of toluene is heated at reflux for about five hours. After this time the reaction mixture is allowed to cool to ambient temperature as it stirred for about 18 hours. The reaction mixture is then concentrated under reduced pressure to a residual oil. The oil is subjected to column chromatography on silica gel, using 1:1 methylene chloride/petroleum ether as the eluant. The product-containing fractions are combined and concentrated under reduced pressure, yielding 2.6 grams of a mixture 5-(4-chlorophenyl)-4-hexenenitrile and 5-(4-chlorophenyl)-5-hexenenitrile. The NMR spectrum is consistent with the proposed structures. This reaction is repeated.

Step C Synthesis of a mixture of 3-cyano-2-oxo-6-(4-chlorophenyl)-5-heptene and 3-cyano-2-oxo-6-(4-chlorophenyl)-6-heptene as intermediates Under a nitrogen atmosphere, a stirred solution of 5.4 grams (0.026 mole) of a mixture 5-(4-chlorophenyl)-4-hexenenitrile and 5-(4-chlorophenyl)-5-hexenenitrile in 75 mL of tetrahydrofuran is cooled to about −80° C., and 11.6 mL (0.029 mole) of n-butyllithium (2.5 molar in hexanes) is added dropwise while maintaining the reaction mixture temperature below −80° C. Upon completion of addition, the reaction mixture is stirred at −80° C. for one hour. After this time a solution of 3.9 mL (0.039 mole) of ethyl acetate in 75 mL of tetrahydrofuran is added dropwise while maintaining the reaction mixture temperature below −80° C. Upon completion of addition, the reaction mixture is allowed to warm to ambient temperature as it stirred for about 18 hours. After this time the reaction mixture is poured into 200 mL of water and made acidic with aqueous 2N hydrochloric acid. The mixture is then extracted with two 200 mL portions of diethyl ether. The combined extracts are dried with magnesium sulfate and filtered. The filtrate is concentrated under reduced pressure, yielding 6.5 grams of a mixture of 3-cyano-2-oxo-6-(4-chlorophenyl)-5-heptene and 3-cyano-2-oxo-6-(4-chlorophenyl)-6-heptene. The NMR spectrum is consistent with the proposed structures.

Step D Synthesis of a mixture of 3-cyano-2-pentoxy-6-(4-chlorophenyl)-2,5-heptadiene and 3-cyano-2-pentoxy-6-(4-chlorophenyl)-2,6-heptadiene as intermediates In a reaction vessel fitted with a Dean-Stark trap to collect the water by product, and under a nitrogen atmosphere, a stirred solution of 6.5 grams (0.026 mole) of a mixture of 3-cyano-2-oxo-6-(4-chlorophenyl)-5-heptene and 3-cyano-2-oxo-6-(4-chlorophenyl)-6-heptene, 10 mL (0.091 mole) of 1-pentanol, and 0.5 gram of p-toluenesulfonic acid in 100 mL of toluene is heated at reflux for about 21 hours. After this time the reaction mixture is concentrated under reduced pressure to a residual oil. The oil is subjected to column chromatography on silica gel, using methylene chloride as the eluant. The product-containing fractions are combined and concentrated under reduced pressure, yielding 7.2 grams of a mixture of 3-cyano-2-pentoxy-6-(4-chlorophenyl)-2,5-heptadiene and 3;cyano-2-pentoxy-6-(4-chlorophenyl)-2,6-heptadiene. The NMR spectrum is consistent with the proposed structures.

Step E Synthesis of trans-2,4-diamino-6-methyl-5-[3-(4-chlorophenyl)-1-butenyl]pyrimidine (Compound 7) and trans-2,4-diamino-6:methyl-5-[3-(4-chlorophenyl)-2-butenyl]pyrimidine (Compound 34)

A solution of 3.8 grams (0.039 mole) of guanidine hydrochloride in 40 mL of ethanol is stirred, and 2.3 grams (0.039 mole) of sodium methoxide is added in one portion. Upon completion of addition, the reaction mixture is stirred at ambient temperature for one hour. After this time the reaction mixture is concentrated under reduced pressure to a residual solid. The solid is then taken up in 20 mL of N,N-dimethylacetamide, and 3.6 grams (0.011 mole) of a mixture of 3-cyano-2-pentoxy-6-(4-chlorophenyl)-2,5-heptadiene and 3-cyano-2-pentoxy-6-(4-chlorophenyl)-2,6-heptadiene is added. Under a nitrogen atmosphere, the reaction mixture is then warmed to 150° C. where it is stirred for 24 hours. After this time the reaction mixture is allowed to cool to ambient temperature where it is stirred for about 60 hours. The reaction mixture is then concentrated under reduced pressure to a residue. The residue is stirred with a mixture of methylene chloride and methanol and allowed to stand for about 24 hours. The resultant off-white solid is collected by filtration. An NMR spectrum of the solid indicates that it is predominantly the 2-butene derivative. The solid is adsorbed onto sodium sulfate and subjected to column chromatography on silica gel, using 10% methanol in methylene chloride as the eluant. The product-containing fractions are combined and concentrated under reduced pressure, yielding 0.4 gram of trans-2,4-diamino-6-methyl-5-[3-(4-chlorophenyl)-2-butenyl]pyrimidine (Compound 34). The NMR spectrum is consistent with the proposed structure. A 0.2 gram sample of crude trans-2,4-diamino-6-methyl-5-[3-(4-chlorophenyl)-1-butenyl]pyrimidine isolated from a previous reaction is combined with the methanol-methylene chloride filtrate from above. The mixture is subjected to column chromatography on silica gel, using 10% methanol in methylene chloride as the eluant. The product-containing fractions are combined and concentrated under reduced pressure, yielding 0.3 gram of trans-2,4-diamino-6-methyl-5-[3-(4-chlorophenyl)-1-butenyl] pyrimidine, mp 158°-165° C. (Compound 7). The NMR spectrum is consistent with the proposed structure.

Example 2

SYNTHESIS OF 2,4-DIAMINO-6-METHYL-5-[3-(2,5-DICHLOROPHENYL)-2-BUTENYL] PYRIMIDINE (COMPOUND 35)

Step A Synthesis of 3-hydroxy-3-(2,5-dichlorophenyl)-1-butene as an intermediate Under a nitrogen atmosphere, a stirred solution of 6.9 grams (0.053 mole) of vinylmagnesium bromide in 50 mL of tetrahydrofuran is cooled to 10°-15° C., and 10.0 grams (0.053 mole) of 2,5-dichloroacetophenone is added dropwise during a 20 minute period. Upon completion of addition the reaction mixture temperature is maintained at 10°-15° C. for two hours. After this time the reaction mixture is poured into 100 mL of cold aqueous 10% hydrochloric acid solution. The mixture is shaken with 100 mL of diethyl ether, and the organic layer is separated. The aqueous layer is extracted with two 50 mL portions of diethyl ether. The combined organic layers are washed with one 50 mL portion of aqueous 5% hydrochloric acid solution and then with two 30 mL portions of an aqueous solution saturated with sodium chloride. The organic layer is dried with magnesium sulfate and filtered. The filtrate is concentrated under reduced pressure, yielding 12.3 grams of 3-hydroxy-3-(2,5-dichlorophenyl)-1-butene. The NMR spectrum is consistent with the proposed structure.

Step B Synthesis of 1-chloro-3-(2,5-dichlorophenyl)-2-butene as an intermediate

Under a nitrogen atmosphere, a stirred solution of 12.0 grams (0.056 mole) of 3-hydroxy-3-(2,5-dichlorophenyl)-1-butene and 4.7 grams (0.056 mole) of pyridine in 85 mL of methylene chloride is cooled in an ice-water bath, and 6.6 grams (0.056 mole) of thionyl chloride is added dropwise. Upon completion of addition, the reaction mixture is stirred for about one hour. After this time the reaction mixture is diluted with 50 mL of methylene chloride and about 50 grams of ice. The mixture is stirred until the ice melts, and then the organic layer is separated. The organic layer is washed in turn with two 50 mL portions of an aqueous 0.5M solution of hydrochloric acid, two 50 mL portions of an aqueous solution saturated with sodium bicarbonate, two 50 mL portions of water, and two 50 mL portions of an aqueous solution saturated with sodium chloride. The organic layer is then dried with magnesium sulfate and filtered. The filtrate is concentrated under reduced pressure, yielding 5.5 grams of 1-chloro-3-(2,5-dichlorophenyl)-2-butene. The NMR spectrum is consistent with the proposed structure.

Step C Synthesis of ethyl 2-methylcarbonyl-5-(2,5-dichlorophenyl)-4-hexenoate as an intermediate Under a nitrogen atmosphere, a mixture of 0.8 gram (0.021 mole) of sodium hydride (60% in mineral oil) in 40 mL of ethanol is stirred for about 15 minutes, and a solution of 2.8 grams (0.021 mole) of ethyl acetoacetate in 5 mL of ethanol is added dropwise. Upon completion of addition, the reaction mixture is stirred at ambient temperature for one hour. After this time a solution of 5.0 grams (0.021 mole) of 1-chloro-3-(2,5-dichlorophenyl)-2-butene in 10 mL of ethanol is added dropwise. Upon completion of addition, the reaction mixture is stirred at ambient temperature for about 18 hours. The reaction mixture is then concentrated under reduced pressure to a residue. The residue is stirred with 50 mL of an aqueous 10% acetic acid solution and then is extracted with two 30 mL portions of diethyl ether. The combined extracts are washed with an aqueous solution saturated with sodium chloride. The organic layer is dried with magnesium sulfate and filtered. The filtrate is concentrated under reduced pressure to a residue. The residue is subjected to column chromatography on silica gel, using petroleum ether as the eluant. The product-containing fractions are combined and concentrated under reduced pressure, yielding 5.2 grams of ethyl 2-methylcarbonyl-5-(2,5-dichlorophenyl)-4-hexenoate. The NMR spectrum is consistent with the proposed structure.

Step D Synthesis of 2-amino-4-hydroxy-6-methyl-5-[3-(2,5-dichlorophenyl)-2-butenyl]pyrimidine as an intermediate Under a nitrogen atmosphere, a solution of 5.0 grams (0.015 mole) of ethyl 2-methylcarbonyl-5-(2,5- dichlorophenyl)-4-hexenoate in 70 mL of ethanol is stirred, and 3.1 grams (0.032 mole) of guanidine hydrochloride is added. To this is then added dropwise a mixture of 1.5 grams (0.038 mole) of sodium hydride (60% in mineral oil) in 30 mL of ethanol. Upon completion of addition, the reaction mixture is warmed to reflux where it is stirred for about 18 hours. After this time the reaction mixture is cooled and concentrated under reduced pressure to a residual oil. The oil is stirred with 40 mL of aqueous 10% acetic acid, and the acid wash is decanted from the oil. This is repeated with an additional 40 mL of aqueous 10% acetic acid, and then with two 30 mL portions of water. The oil is dissolved in hot ethanol and the solution is placed in a refrigerator. The resultant solid is collected by filtration, yielding 4.7 grams of 2-amino-4-hydroxy-6-methyl-5-[3-(2,5-dichlorophenyl)-2-butenyl]pyrimidine, mp>250° C. The NMR spectrum is consistent with the proposed structure.

Step E Synthesis of 2-amino-4-chloro-6-methyl-5-[3-(2,5-dichlorophenyl)-2-butenyl]pyrimidine as an intermediate Under a nitrogen atmosphere, a stirred solution of 2.0 grams (0.006 mole) of 2-amino-4-hydroxy-6-methyl-5-[3-(2,5-dichlorophenyl)-2-butenyl]pyrimidine, 16.5 grams (0.107 mole) of phosphorus oxychloride, and 1.5 grams (0.007 mole) of phosphorus pentachloride is heated at reflux for about 18 hours. After this time the reaction mixture is slowly pipetted into wet ice during a 20 minute period. The mixture is then stirred until the ice melted, and the resultant solid is collected by filtration. The solid is dissolved in methylene chloride, and the solution is dried with magnesium sulfate. The mixture is filtered and the filtrate is concentrated under reduced pressure, yielding 2.0 grams of 2-amino-4-chloro-6-methyl-5-[3-(2,5-dichlorophenyl)-2-butenyl]pyrimidine; mp 97°–100° C. The NMR spectrum is consistent with the proposed structure.

Step F Synthesis of 5-amino-7-methyl-8-[3-(2,5-dichlorophenyl)-2-butenyl]tetrazolo[1,5-c]pyrimidine as an intermediate Under a nitrogen atmosphere, a solution of 2.0 grams (0.006 mole) of 2-amino-4-chloro-6-methyl-5-[3-(2,5-dichlorophenyl)-2-butenyl]pyrimidine, 0.4 gram (0.006 mole) of sodium azide, and 0.3 gram (0.006 mole) of ammonium chloride in 15 mL of dimethyl sulfoxide is stirred at ambient temperature for about 18 hours. After this time the reaction mixture is poured into ice-water. The mixture is stirred until the ice melted, and the resultant solid is collected by filtration. The solid is dissolved in methylene chloride, and the solution is dried with magnesium sulfate. The mixture is filtered, and the filtrate is concentrated under reduced pressure to a residual solid. The solid is recrystallized from methylene chloride/petroleum ether, yielding 1.8 grams of 5-amino-7-methyl-8-[3-(2,5-dichlorophenyl)-2-butenyl]tetrazolo[1,5-c]-pyrimidine. The NMR spectrum is consistent with the proposed structure.

Step G Synthesis of 2,4-diamino-6-methyl-5-[3-(2,5-dichlorophenyl)-2- butenyl]pyrimidine (Compound 35)

Zinc is activated by treating 2.5 grams (excess) of it with aqueous 10% hydrochloric acid for two minutes. The activated zinc is collected by filtration, washed with water then acetone, and dried in a vacuum oven for one hour. A solution of 1.5 grams (0.004 mole) of 5-amino-7-methyl-8-[3-(2,5-dichlorophenyl)-2-butenyl]tetrazolo[1,5-c]pyrimidine in 35 mL of acetic acid is stirred, and the activated zinc is added portionwise during a 20 minute period. Upon completion of addition, the reaction mixture is warmed to about 80° C. where it is stirred for about 18 hours. After this time, the reaction mixture is stirred with 50 mL of water. The mixture is then extracted with three 30 mL portions of methylene chloride. The combined extracts are washed with two 10 mL portions of an aqueous solution saturated with sodium bicarbonate. The organic layer is dried with magnesium sulfate and filtered. The filtrate is concentrated under reduced pressure to a residue. The residue is subjected to column chromatography on silica gel; using 15% methanol in methylene chloride as the eluant. The product-containing fractions are combined and concentrated under reduced pressure, yielding 0.4 gram of 2,4-diamino-6-methyl-5-[3-(2,5-dichlorophenyl)-2-butenyl]pyrimidine; mp 172°–174° C. The NMR spectrum is consistent with the proposed structure.

Example 3

SYNTHESIS OF 2,4-DIAMINO-6-METHYL-5-(3-PHENYL-1-PROPYNYL)PYRIMIDINE (COMPOUND 39)

Step A Synthesis of 2,4-diamino-6-methylpyrimidine as an intermediate

A mixture of 50.0 grams (0.348 mole) of 2-amino-4-chloro-6-methylpyrimidine (commercially available) and 100 mL of aqueous 30% ammonia in 400 mL of methanol is placed in a high pressure vessel and heated to 130°–165° C. under a pressure of 140–250 psig, where it is stirred for 13 hours. After this time, the reaction mixture is allowed to cool to ambient temperature. The reaction vessel is then opened and the reaction mixture is removed. The reaction vessel is washed with 200 mL of methanol, and the wash is combined With the reaction mixture. The combination is concentrated under reduced pressure to a residual solid. The solid is then stirred for 2 hours at ambient temperature with 100 mL of aqueous 30% ammonia. The mixture is cooled to 0° C., and the solid is collected by filtration. The solid is dried, yielding 40.8 grams of 2,4-diamino-6-methylpyrimidine. The NMR spectrum is consistent with the proposed structure.

Step B Synthesis of 2,4-diamino-5-iodo-6-methylpyrimidine as an intermediate

A solution of 8.0 grams (0.064 mole) of 2,4-diamino-6-methylpyrimidine in 30 mL of glacial acetic acid is stirred, and a solution of 13.5 grams (0.083 mole) of iodine monochloride in 20 mL of glacial acetic acid is added drop-wise during a 5 minute period. Upon completion of addition, the reaction mixture is stirred at ambient temperature for about 18 hours. After this time the reaction mixture is diluted with 100 mL of water and then is made basic with 10% aqueous sodium hydroxide. The mixture is then extracted with three 75 mL portions of ethyl acetate. The combined extracts are washed with one 75 mL portion of an aqueous solution saturated with sodium chloride. The organic layer is added with sodium sulfate and filtered. The filtrate is concentrated under reduced pressure, yielding 11.7 grams of 2,4-diamino-5-iodo-6-methylpyrimidine. The NMR spectrum is consistent with the proposed structure.

Step C Synthesis of 2,4-diamino-6-methyl-5-(3-phenyl-1-propynyl)pyrimidine pyrimidine (Compound 39)

A reaction vessel containing 0.8 gram (0.0032 mole) of 2,4-diamino-5-iodo-6-methylpyrimidine, 0.5 mL (0.0042 mole) of 3-phenyl-1-propyne, 0.2 gram (catalyst) of bis(triphenylphosphine)palladium(II) chloride, 0.05 gram (catalyst) of copper iodide, and 8 mL of triethylamine is evacuated and refilled with dry nitrogen gas three times. The reaction mixture is then stirred at ambient temperature for about 60 hours. After this time, the reaction mixture is diluted with 100 mL of water. The mixture is then extracted with three 75 mL portions of ethyl acetate. The combined extracts are washed with three 75 mL portions of an aqueous 5% lithium chloride solution. The organic layer is dried with sodium sulfate and filtered. The filtrate is concentrated under reduced pressure to a residue. The residue is subjected to column chromatography on silica gel, using 5–15% methanol methylene chloride mixtures as eluants. The appropriate product-containing fractions are combined and concentrated under reduced pressure, yielding 0.3 gram of 2,4-diamino-6-methyl-5-(3-phenyl-1-propynyl)pyrimidine. The NMR spectrum is consistent with the proposed structure. Other fractions containing less pure product are combined and concentrated under reduced pressure to a residue. This residue is subjected to column chromatography on neutral alumina, using 2.5–10% methanol in methylene Chloride mixtures as eluants. The product-containing fractions are combined and concentrated under reduced pressure, yielding an additional 0.2 gram of 2,4-diamino-6-methyl-5-(3-phenyl-1-propynyl)pyrimidine. The NMR spectrum is consistent with the proposed structure. The two solids are combined, yielding about 0.5 gram of 2,4-diamino-6-methyl-5-(3-phenyl-1-propynyl)pyrimidine, mp 145°–149° C.

Example 4

SYNTHESIS OF 2,4-DIAMINO-6-METHYL-5-[3,3-DIFLUORO-3-(4-CHLOROPHENYL)-1-PROPENYL]PYRIMIDINE (COMPOUND 4)

Step A Synthesis of 2,2-difluoro-2-(4-chlorophenyl)ethanol as an intermediate

Lithium aluminum hydride, 2.4 grams (0.063 mole), is placed in a reaction vessel, and 200 mL of diethyl ether is added dropwise with stirring. To this is added dropwise a solution of 22.8 grams (0.097 mole) of ethyl 4-chlorophenyldifluoroacetate (prepared by methods taught by W. J. Middleton et al., J. Org. Chem., (1980), 45, 2883–2887) in 100 mL of diethyl ether, while maintaining the reaction mixture temperature at about 25° C. Upon completion of addition, the reaction mixture is stirred at ambient temperature for about 36 hours. The reaction is then quenched by the careful dropwise addition of an aqueous solution of 10% sodium hydroxide. The reaction mixture is slowly made acidic with aqueous 2N hydrochloric acid and then is diluted with 200 mL of water. The organic layer is separated, and the aqueous layer is washed with two 300 mL portions of diethyl ether. The organic layer and the diethyl ether washes are combined and washed with one 250 mL portion of an aqueous solution saturated with sodium chloride. The organic layer is dried with magnesium sulfate and filtered. The filtrate is concentrated under reduced pressure, yielding 2,2-difluoro-2-(4-chlorophenyl)ethanol.

Step B Synthesis of difluoro-4-chlorophenylacetaldehyde as an intermediate

A stirring solution of 7.0 grams (0.055 mole) of oxalyl chloride in 125 mL of methylene chloride is cooled to –60° C., and a solution of 9.5 grams (0.120 mole) of dimethyl sulfoxide in 25 mL of methylene chloride is added dropwise during a five minute period. Upon completion of addition, the reaction mixture is stirred at –60° C. for about 10 minutes, and then a solution of 9.6 grams (0.050 mole) of 2,2-difluoro-2-(4-chlorophenyl)ethanol in 25 mL of methylene chloride is added dropwise during a five minute period. Upon completion of addition, the reaction mixture is stirred for 15 minutes, and 25.5 grams (0.250 mole) of triethylamine is added while maintaining the reaction mixture temperature at –60° C. Upon completion of addition, the reaction mixture is allowed to warm to ambient temperature, and 150 mL of water is added. The mixture is stirred for 10 minutes, and the organic layer is separated. The aqueous layer is washed with 100 mL of methylene chloride. The methylene chloride wash and the organic layer are combined, and the combination is washed with 100 mL of water and then with 100 mL of an aqueous solution saturated with sodium chloride. The organic layer is dried with magnesium sulfate and filtered. The filtrate is concentrated under reduced pressure, yielding difluoro-4-chlorophenylacetaldehyde.

NOTE: The procedure to prepare difluoro-4-chlorophenylacetaldehyde as shown in Step B above is disclosed by D. Swern et al., Tetrahedron, (1978),34, 1651–1660.

Step C Synthesis of 1,1-difluoro-1-(4-chlorophenyl)-3-iodo-2-propene as an intermediate Under a nitrogen atmosphere, a stirred suspension of 29.5 grams (0.24 mole) of anhydrous chromium(II) dichloride in 400 mL of tetrahydrofuran is cooled to 0° C., and a solution of 7.6 grams (0.04 mole) of difluoro-4-chlorophenylacetaldehyde and 31.5 grams (0.08 mole) of iodoform in 200 mL of tetrahydrofuran is added dropwise. Upon completion of addition, the reaction mixture is stirred at 0° C. for three hours. After this time the reaction mixture is poured into about 1200 mL of water, and the mixture is extracted with three 150 mL portions of diethyl ether. The combined extracts are dried with sodium sulfate and filtered. The filtrate is concentrated under reduced pressure, yielding 1,1-difluoro-1-(4-chlorophenyl)-3-iodo-2-propene.

NOTE: The procedure to prepare 1,1-difluoro-1-(4-chlorophenyl)-3-iodo-2-propene as shown in Step C above is disclosed by K. Takai et al., JACS, (1986), 108, 7408.

Step D Synthesis of 1,1-difluoro-1-(4-chlorophenyl)-3-tributylstannyl-2-propene as an intermediate.

Under a nitrogen atmosphere, a stirred mixture of 9.8 grams (0.030 mole) of hexabutylditin, 7.9 grams (0.025 mole) of 1,1-difluoro-1-(4-chlorophenyl)-3-iodo-2-propene, and 0.3 gram of tetrakis(triphenylphosphine)palladium(0) in 50 mL of toluene is heated at reflux for about five hours. After this time the reaction mixture is cooled and filtered. The filtrate is concentrated under reduced pressure to a residue. The residue is dissolved in diethyl ether and washed several times with water. The organic layer is dried with magnesium sulfate and filtered. The filtrate is concentrated under reduced pressure, yielding 1,1-difluoro-1-(4-chlorophenyl)-3-tributylstannyl-2-propene NOTE: The procedure to prepare 1,1-difluoro-1-(4-chlorophenyl)-3-tributylstannyl-2-propene as shown in Step D above is disclosed by H. Azizian et al., J. Organometallic Chem., (1981), 215, 49–58.

Step E Synthesis of 2,4-diamino-6-methyl-5-[3,3-difluoro-3-(4-chlorophenyl)-1-propenyl]pyrimidine (Compound 4)

A mixture of 0.04 gram (catalyst) of tri-2-furylphosphine and 0.04 gram (catalyst) of tris(dibenzylidineacetone) dipalladium(0) in 30 mL of N,N-dimethylformamide is purged with dry nitrogen gas and stirred at ambient temperature for five minutes. After this time 1.2 grams (0.0048 mole) of 2,4-diamino-5-iodo-6-methylpyrimidine (prepared in Step B of Example 3) is added in one portion. The reaction vessel is then immersed in an oil bath that is preheated to 60° C. where it is maintained for about five minutes. After this time, 3.1 grams (0.0064 mole) of 1,1-difluoro-1-(4-chlorophenyl)-3-tributylstannyl-2-propene is added in one portion to the reaction mixture. The reaction mixture is again purged with dry nitrogen gas, and the oil bath temperature is brought to 80°–85° C. where it is maintained for about 18 hours. After this time the reaction mixture is diluted with 200 mL of water and extracted with two 200 mL portions of ethyl acetate. The combined extracts are then washed with three 100 mL portions of an aqueous solution of 5% lithium chloride. The organic layer is concentrated under reduced pressure to a residue. The residue is purified by column chromatography, yielding 2,4-diamino-6-methyl-5-[3,3-difluoro-3-(4-chlorophenyl)-1-propenyl] pyrimidine.

NOTE: The procedure to prepare 2,4-diamino-6-methyl-5-[3,3-difluoro-3-(4-chlorophenyl)-1-propenyl]pyrimidine as shown in Step E above is disclosed by V. Farina et al., JACS, (1991), 113, 9585–9595.

Example 5

SYNTHESIS OF 2,4-DIAMINO-6-METHYL-5-[3-(4—CHLOROPHENYL)-3-OXO-1-PROPENYL] PYRIMIDINE (COMPOUND 27)

Step A Synthesis of 1-oxo-1-(4-chlorophenyl)-3-iodo-2-propene as an intermediate This compound is prepared in a manner analogous to that of Step C of Example 4, using 6.7 grams (0.04 mole) of 4-chlorophenylglyoxal (prepared by the method of Kornblum et al., JACS, (1957), 79, 6562), 29.5 grams (0.24 mole) of anhydrous chromium(II) dichloride, and 31.5 grams (0.08 mole) of iodoform in 600 mL of tetrahydrofuran, yielding 1-oxo-1-(4-chlorophenyl)-3-iodo-2-propene.

Step B Synthesis of 1-oxo-1-(4-chlorophenyl)-3-tributylstannyl-2-propene as an intermediate This compound is prepared in a manner analogous to that of Step D of Example 4, using 9.8 grams (0.030 mole) of hexabutylditin, 7.3 grams (0.025 mole) of 1-oxo-1-(4-chlorophenyl)-3-iodo-2-propene, and 0.3 gram (catalyst) of tetrakis(triphenylpliosphine)palladium(0) in 50 mL of toluene, yielding 1-oxo-1-(4-chlorophenyl)-3-tributylstannyl-2-propene.

Step C Synthesis of 2,4-diamino-6-methyl-5-[3-(4-chlorophenyl)-3-oxo-1-propenyl]pyrimidine (Compound 27)

This compound is prepared in a manner analogous to that of Step E of Example 4, using 2.9 grams of (0.0064 mole) of 1-oxo-1-(4-chlorophenyl)-3tributylstannyl-2-propene, 1.2 grams (0.0048 mole) of 2,4-diamino-5-iodo-6-methylpyrimidine (prepared in Step B Example 3), 0.04 gram of tri-2-furylphosphine and 0.04 gram (catalyst) of tris(dibenzylidineacetone)dipalladium(0) in 30 mL of N,N-dimethylformamide, yielding 2,4-diamino-6-methyl-5-[3-(4-chlorophenyl)-3-oxo-1-propenyl]pyrimidine.

Example 6

SYNTHESIS OF 2,4-DIAMINO-6-METHYL-5-[3-(4-FLUORO PHENYL)-3-METHYL-1-BUTENYL] PYRIMIDINE (COMPOUND 66)

Step A Synthesis of 3-(4-fluorophenyl)-3-methylbutyraldehyde as an intermediate

Under a nitrogen atmosphere, a stirring solution of 66.6 grams (0.334 mole) of 4-fluorophenylmagnesium bromide (1M in diethyl ether) is cooled to −10° C., and 2.2 grams (0.015 mole) of copper(I) bromide is added in one portion. Upon completion of addition, a solution of 25.0 grams (0.297 mole) of 3-methyl-2-butenal in 20 mL of tetrahydrofuran is added dropwise at a rate to maintain the reaction mixture temperature at about 5° C. The complete addition requires about one hour. Upon completion of addition, the reaction mixture is stirred for one additional hour and then is stored in a refrigerator for about 18 hours. After this time the reaction mixture is poured into 500 mL of aqueous ammonium chloride and extracted with four portions of diethyl ether. The combined extracts are concentrated under reduced pressure to a residue. The residue is subjected to column chromatography on silica gel, using methylene chloride as the eluant. The product-containing fractions are combined and concentrated under reduced pressure to a residue. The residue is subjected to a second column chromatography on silica gel, using 100% petroleum ether and combinations of methylene chloride in petroleum ether. The product-containing fractions are combined and concentrated under reduced pressure, yielding about 23.0 grams of 3-(4-fluorophenyl)-3-methylbutyraldehyde. The NMR spectrum is consistent with the proposed structure.

Step B Synthesis of 3-(4-fluorophenyl)-3-methyl-1-tributylstannylbutanol as an intermediate A stirring solution of 10.8 mL (0.077 mole) of diisopropylamine in 100 mL of tetrahydrofuran is cooled to 0° C., and 30.8 mL (0.077 mole) of n-butyl-lithium (2.5M in hexanes) is added dropwise. Upon completion of the addition, the reaction mixture is stirred for about 10 minutes, then 22.3 grams (0.077 mole) of tributyltin hydride is added dropwise at a rate to maintain the reaction mixture temperature at about 0° C. The reaction mixture is then stirred for about 15 minutes. After this time the reaction mixture is cooled to −78° C., and a solution of 13.8 grams (0.077 mole) of 3-(4-fluorophenyl)-3-methylbutyraldehyde in about 15 mL of tetrahydrofuran is added dropwise during a 30 minute period. Upon completion of addition, the reaction mixture is stirred at −78° C. for ten minutes. After this time the reaction mixture is quenched by the dropwise addition of 300 mL of aqueous 10% ammonium chloride. The mixture is then extracted with two 200 mL portions of diethyl ether. The combined extracts were dried with magnesium sulfate and filtered. The filtrate is concentrated under reduced pressure, at a temperature of less than 30° C., yielding 36.3 grams of 3-(4-fluorophenyl)-3-methyl-1-tributylstannylbutanol. The NMR spectrum is consistent with the proposed structure.

Step C Synthesis of 3-(4-fluorophenyl)-3-methyl-1-iodo-1-tributylstannylbutane as an intermediate A solution of 30.4 grams (0.116 mole) of triphenylphosphine in about 116 mL of methylene chloride is stirred, and 7.9 grams (0.116 mole) of imidazole is added. Upon completion of addition, the reaction mixture is stirred about one hour until the imidazole dissolves, then 29.4 grams (0.116 mole) iodine is added portionwise. After the iodine dissolves, the reaction mixture is cooled to 0° C., and a solution of 36.3 grams (0.077 mole) of 3-(4-fluorophenyl)-3-methyl-1-tributylstannylbutanol in about 77 mL of methylene chloride is added dropwise, while maintaining the reaction mixture temperature below 0° C. Upon completion of addition, the reaction mixture is allowed to warm to ambient temperature where it is stirred for about 18 hours. The reaction mixture is then taken up in about 500 mL of acetonitrile and extracted with three 300 mL portions of hexane. The combined extracts are concentrated under reduced pressure to a residue. The residue is subjected to column chromatography on silica gel, using petroleum ether as the eluant. The product-containing fractions are combined and concentrated under reduced pressure, yielding 17.8 grams of 3-(4-fluorophenyl)-3-methyl-1-iodo-1-tributylstannylbutane. The NMR spectrum is consistent with the proposed structure.

Step D Synthesis of 3-(4-fluorophenyl)-3-methyl-1-tributylstannyl-1-butene as an intermediate Under a nitrogen atmosphere, a stirred solution of 17.2 grams (0.030 mole) of 3-(4-fluorophenyl)-3-methyl-1-iodo-1-tributylstannylbutane and 13.7 grams (0.090 mole) of 1,8-diazabicyclo[5.4.0]undec-7-ene (DBU)in 100 mL of tetrahydrofuran is heated at reflux for about 18 hours. The reaction mixture is cooled and poured into about 500 mL of water. The mixture is then made acidic with aqueous 2N hydrochloric acid and extracted with three 200 mL portions of diethyl ether. The combined extracts are dried with magnesium sulfate and filtered. The filtrate is concentrated under reduced pressure to a residue. The residue is subjected to column chromatography on silica gel, using 5% methylene chloride in petroleum ether as the eluant. The product-containing fractions are combined and concentrated under reduced pressure, yielding 12.0 grams of 3-(4-fluorophenyl)-3-methyl-1-tributylstannyl-1-butene. The NMR spectrum is consistent with the proposed structure.

NOTE: The procedure to prepare 3-(4-fluorophenyl)-3-methyl-1-tributylstannyl-1-butene as shown in Steps B–D above is disclosed by J. M. Chong et al., JOC, (1993), 58, 523–527.

Step E Synthesis of 2,4-diamino-6-methyl-5-[3-(4-fluorophenyl)-3-methyl-1-butenyl]pyrimidine (Compound 66)

Under a nitrogen atmosphere, a stirring solution of 4.2 grams (0.009 mole) of 3-(4-fluorophenyl)-3-methyl-1-tributylstannyl-1-butene, 1.9 grams (0.077 mole) of 2,4-diamino-5-iodo-6-methylpyrimidine (prepared in Step B of Example 3), 2.0 grams (0.046 mole) of lithium chloride, 0.4 gram (catalyst) of bis(triphenyl phosphine)palladium(II) chloride, and about 0.05 gram (catalyst) of 2,6-di-tert-butyl-4-methylphenol in 80 mL of N,N-dimethylformamide is heated at 65° C. for about 2.5 days. After this time the reaction mixture is cooled and poured into 500 mL of water. The mixture then is extracted with three 100 mL portions of ethyl acetate. The combined extracts are dried with magnesium sulfate and filtered. The filtrate is concentrated under reduced pressure to a residue. The residue is subjected to column chromatography on basic alumina (containing 6% water), using 10% methanol in methylene chloride as the eluant. The product-containing fractions are combined and concentrated under reduced pressure to a residue. NMR analysis of the residue indicates an impure product. The residue is subjected to column chromatography on silica gel, using 10% methanol in methylene chloride as the eluant. The product-containing fractions are combined and concentrated under reduced pressure, yielding about 0.6 gram of 2,4-diamino-6-methyl-5-[3-(4-fluorophenyl)-3-methyl-1-butenyl]pyrimidine, mp 164°–168° C. (Compound 66). The NMR spectrum is consistent with the proposed structure.

Example 7

SYNTHESIS OF 2-ETHYLAMINO-4-AMINO-6-METHYL-5-[3-(4-CHLOROPHENYL)-1-BUTENYL]PYRIMIDINE (COMPOUND 47) AND 2-ETHYLAMINO-4-AMINO-6-METHYL-5-[3-(4-CHLOROPHENYL)-2-BUTENYL]PYRIMIDINE

These compounds are prepared in a manner analogous to that of Step E Of Example 1, using 4.8 grams (0.039 mole) of 1-ethylguanidine hydrochloride, 3.6 grams (0.011 mole) of a mixture of 3-cyano-2-pentoxy-6-(4-chlorophenyl)-2,5-heptadiene and 3-cyano-2-pentoxy-6-(4-chlorophenyl)-2,6-heptadiene (prepared in Steps A–D of Example 1), 2.3 grams (0.039 mole) of sodium methoxide, 20 mL Of N,N-dimethylacetamide, and 40 mL of ethanol. The crude reaction product is subjected to column chromatography, yielding the separated isomers, 2-ethylamino-4-amino-6-methyl-5-[3-(4-chlorophenyl)-1-butenyl]pyrimidine (Compound 47) and 2-ethylamino-4-amino-6-methyl-5-[3-(4-chlorophenyl)-2-butenyl]pyrimidine.

Example 8

SYNTHESIS OF trans-2,4-DI(1-METHYLETHYLCARBONYLAMINO)-6-METHYL-5-[3-(4—CHLOROPHENYL)-1-BUTENYL]PYRIMIDINE (COMPOUND 54)

A stirred mixture of 0.24 gram (0.001 mole) of trans-2,4-diamino-6-methyl-5-[3-(4-chlorophenyl)-1-butenyl]pyrimidine (Compound 7) and 0.01 gram of 4-dimethylaminopyridine in 5 mL of isobutyric anhydride is heated at reflux for about two hours. The mixture is cooled and poured into about 30 mL of water. The mixture is extracted with several portions of ethyl acetate. The combined extracts are washed with water and then dried with magnesium sulfate. The mixture is filtered, and the filtrate is concentrated under reduced pressure, yielding trans-2,4-di(1-methylethylcarbonylamino)-6-methyl-5-[3-(4-chlorophenyl)-1-butenyl]pyrimidine.

Example 9

SYNTHESIS OF 2,4-DIAMINO-6-METHYL-5-[3-(4—CHLOROPHENYL)-3-OXO-1-PROPYNYL]PYRIMIDINE (COMPOUND 46)

This compound is prepared in a manner analogous to that of Step C of Example 3, using 0.8 gram (0.0032 mole) of 2,4-diamino-5-iodo-6-methylpyrimidine, 0.7 gram of (0.0042 mole) of 1-oxo-1-(4-chlorophenyl)-2-propyne (prepared by the method of F. Montanari et al., JCS, (1969), 1204–1208), 0.2 gram of bis(triphenylphosphine)palladium (II) chloride, 0.05 gram of copper iodide, and 8 mL of triethylamine, yielding 2,4-diamino-6-methyl-5-[3-(4-chlorophenyl)-3-oxo-1-propynyl]pyrimidine.

Example 10

SYNTHESIS OF 2,4-DIAMINO-6-METHYL-5-[(4-CHLOROPHENYL)DIMETHYLSILYLETHYNYL]PYRIMIDINE (COMPOUND 45)

This compound is prepared in a manner analogous to that of Step C of Example 3, using 0.8 gram (0.0032 mole) of 2,4-diamino-5-iodo-6-methylpyrimidine, pyrimidine, 0.8 gram of (0.0042 mole) of ethynyl(4-chlorophenyl)dimethylsilane (prepared by the method of M. G. Voronkov et al., Zhurnal Obshchei Khimii, (1982), 52, 1824–1828), 0.2 gram of bis(triphenylphosphine)palladium(II) chloride, 0.05 gram of copper iodide, and 8 mL of piperidine, yielding 2,4-diamino-6-methyl-5-[(4-chlorophenyl)dimethylsilylethynyl]pyrimidine. pyrimidine.

Example 11

SYNTHESIS OF 2,4-DIAMINO-6-METHYL-5-[2-[1-(4—CHLOROPHENYL)-1-CYCLOPENTYL]ETHENYL]PYRIMIDINE (COMPOUND 24)

Step A Synthesis of [1-(4-chlorophenyl)-1-cyclopentyl]methanol as an intermediate This compound is prepared in a manner analogous to that of Step A of Example 4, using 2.4 grams (0.063 mole) of lithium aluminum hydride, 21.8 grams (0.097 mole) of 1-(4-chlorophenyl)-1-cyclopentanecarboxylic acid (commercially available) in about 300 mL of diethyl ether, yielding [1-(4-chlorophenyl)-1-cyclopentyl]methanol.

Step B Synthesis of 1-(4-chlorophenyl)-1-cyclopentanecarboxaldehyde as an intermediate This compound is prepared in a manner analogous to that of Step B of Example 4, using 7.0 grams (0.055 mole) of oxalyl chloride, 9.5 grams (0.120 mole) of dimethyl sulfoxide, 10.5 grams (0.050 mole) of [1-(4-chlorophenyl)-1-cyclopentyl]methanol, and 25.5 grams (0.250 mole) of triethylamine in 175 mL of methylene chloride, yielding 1-(4-chlorophenyl)-1-cyclopentanecarboxaldehyde.

Step C Synthesis of 1-(chlorophenyl)-1-(2-iodoethenyl)cyclopentane as an intermediate This compound is prepared in a manner analogous to that of Step C of Example 4, using 29.5 grams (0.24 mole) of anhydrous chromium(II) dichloride, 8.3 grams (0.04 mole) of 1-(4-chlorophenyl)-1-cyclopentanecarboxaldehyde, and 31.5 grams (0.08 mole) of iodoform in about 600 mL of tetrahydrofuran, yielding 1-(chlorophenyl)-1-(2-iodoethenyl)cyclopentane.

Step D Synthesis of 1-(chlorophenyl)-1-(2-tributylstannylethenyl)cyclopentane as an intermediate This compound is prepared in a manner analogous to that of Step D of Example 4, using 9.8 grams (0.030 mole) of hexabutylditin, 8.1 grams (0.025 mole) of 1-(chlorophenyl)-1-(2-iodoethenyl)cyclopentane, and 0.3 gram of tetrakis(triphenylphosphine)palladium(0) in 50 mL of toluene, yielding 1-(chlorophenyl)-1-(2-tributylstannylethenyl)cyclopentane.

Step E Synthesis of 2,4-diamino-6-methyl-5-[2-[1-(4-chlorophenyl)-1-cyclopentyl]ethenyl]pyrimidine (Compound 24)

This compound is prepared in a manner analogous to that of Step E of Example 4, using 0.04 gram of tri-2-furylphosphine, 0.04 gram (catalyst) of tris(dibenzylidineacetone)dipalladium(0), 1.2 grams (0.0048 mole) of 2,4-diamino-5-iodo-6-methylpyrimidine, and 3.2 grams (0.0064 mole) of 1-(chlorophenyl)-1-(2-tributylstannylethenyl)cyclopentane in 30 mL of N,N-dimethylformamide, yielding 2,4-diamino-6-methyl-5-[2-[1-(4-chlorophenyl)-1-cyclopentyl]ethenyl]pyrimidine, mp 163°–165° C. (Compound 24).

Example 12

SYNTHESIS OF 2-ETHYLAMINO-4-METHYLCARBONYLAMINO-6-METHYL-5-[3-(4-CHLOROPHENYL)-1-BUTENYL]PYRIMIDINE (COMPOUND 58)

This compound is prepared in a manner analogous to that of Example 8, using 0.32 gram (0.001 mole) 2-ethylamino-4-amino-6-methyl-5-[3-(4-chlorophenyl)-1-butenyl]pyrimidine (Compound 47-prepared in Example 7) and 0.01 gram (catalyst) of 4-dimethylaminopyridine in 5 mL of acetic anhydride, yielding 2-ethylamino-4-methylcarbonylamino-6-methyl-5-[3-(4-chlorophenyl)-1-butenyl]pyrimidine.

Example 13

SYNTHESIS OF 2,4-DIAMINO-6-METHYL-5-[1-FLUORO-3-METHYL-3-(4-CHLOROPHENYL)-1-BUTENYL]PYRIMIDINE (COMPOUND 62)

Step A Synthesis of 3-(4-chlorophenyl)-3-methylbutyraldehyde as an intermediate

Under a nitrogen atmosphere, a stirred solution of 21.6 grams (0.10 mole) of 4-chlorophenylmagnesium bromide (1M in diethyl ether) in 100 mL of tetrahydrofuran is cooled to −15° C., and 0.7 grams (catalyst) of copper(I) bromide is added in one portion. Upon completion of addition, 9.7 mL (0.10 mole) of 3-methyl-2-butenal is added dropwise during a 1.5 hour period, while maintaining the reaction mixture temperature below −10° C. Upon completion of addition, the reaction mixture is allowed to warm to ambient temperature, where it is stirred for about 18 hours. The reaction mixture is then poured into 300 mL of water and extracted with two 200 mL portions of diethyl ether. The combined extracts are dried with magnesium sulfate and filtered. The filtrate is concentrated under reduced pressure to a residue. The residue, is subjected to column chromatography on silica gel, using 50% petroleum ether in methylene chloride as the eluant. The appropriate product-containing containing fractions are combined and concentrated under reduced pressure, yielding 7.6 grams of 3-(4-chlorophenyl)-3-methylbutyraldehyde. The NMR spectrum is consistent with the proposed structure. The reaction is repeated.

Step B Synthesis of 1-fluoro-1-phenylsulfonyl-3-methyl-3-(4-chlorophenyl)-1-butene as an intermediate Under a nitrogen atmosphere, 25.0 grams (0.14 mole) of distilled fluoromethyl phenyl sulfone (prepared by the method of J. R McCarthy et al., Org. Syn. 1993, 72, 209), 24.8 grams (0.14 mole) of diethyl chlorophosphate, and 300 mL of anhydrous tetrahydrofuran are placed in a reaction vessel. The stirring mixture is cooled to about −70° C., and a solution of 310 mL (0.31 mole) of lithium bis(trimethylsilyl)amide (commercially available-1M in tetrahydrofuran) is added dropwise during a 15 minute period. Upon completion of addition, the reaction mixture is stirred at about −70° C. for one hour. After this time a solution of 19.7 grams (0.10 mole) of 3-(4-chlorophenyl)-3-methylbutyraldehyde in 65 mL of tetrahydrofuran is added via a syringe. Upon completion of addition, the reaction mixture is allowed to warm to ambient temperature where it is stirred for about two hours. The reaction mixture is then poured into an ice-cold mixture of 250 mL of ethyl acetate, 250 mL of saturated aqueous ammonium chloride, and 30 mL. of concentrated hydrochloric acid. The organic layer is separated, and the aqueous layer is extracted with ethyl acetate. The extract and the organic layer are combined, washed with 100 mL of saturated aqueous sodium chloride, and added with magnesium sulfate. The mixture is filtered, and the filtrate is concentrated under reduced pressure to a residue. The residue is subjected to column chromatography on silica gel. The product-containing fractions are combined and concentrated under reduced pressure, yielding 1-fluoro-1-phenylsulfonyl-3-methyl-3-(4-chlorophenyl)-1-butene.

Step C Synthesis of 1-fluoro-3-(4-chlorophenyl)-3-methyl-1-tributylstannyl-1-butene as an intermediate Under a nitrogen atmosphere, a stirring solution of 22.7 grams (0.067 mole) of 1-fluoro-1-phenylsulfonyl-3-methyl-3-(4-chlorophenyl)-1-butene, 42.0 grams (0.14 mole) of tributyltin hydride, and 0.5 gram (catalyst) of azobisisobutyronitrile in 700 mL of cyclohexane is heated at reflux for about three hours. After this time the reaction mixture is cooled to ambient temperature, and 125 mL of silica gel is added. The mixture is concentrated under reduced pressure, and the residue is subjected to column chromatography. The product-containing fractions are combined and concentrated under reduced pressure, yielding 1-fluoro-3-(4-chlorophenyl)-3-methyl-1-tributylstannyl-1-butene.

Step D Synthesis of 2,4-diamino-6-methyl-5-[1-fluoro-3-methyl-3-(4-chlorophenyl)-1-butenyl]pyrimidine (Compound 62)

This compound is prepared in a manner analogous to that of Step E of Example 4, using 1.2 grams (0.0048 mole) of 2,4-diamino-5-iodo-6-methylpyrimidine, 2.3 grams (0.0048 mole) of 1-fluoro-3-(4-chlorophenyl)-3-methyl-1-tributylstannyl-1-butene, 0.04 gram of tri-2-furylphosphine, 0.04 gram of tris(dibenzylidineacetone)dipalladium(0) in about 30 mL of N,N-dimethylformamide, yielding 2,4-diamino-6-methyl-5-[1-fluoro-3-methyl-3-(4-chlorophenyl)-1-butenyl]pyrimidine.

Example 14

SYNTHESIS OF 2,4-DIAMINO-6-METHYL-5-[3-(4-CHLOROPHENYL)-3-METHYL-1-BUTENYL] PYRIMIDINE (COMPOUND 21)

Step A Synthesis of 2-methyl-2-(4-chlorophenyl)propanol as an intermediate

A stirring mixture of 5.4 grams (0.136 mole) of lithium aluminum hydride in 300 mL of diethyl ether is cooled in an ice-water bath, and a solution of 45.0 grams (0.226 mole) of 2-methyl-2-(4-chlorophenyl)propanoic acid in 300 mL of diethyl ether is added dropwise during a one hour period. Upon completion of addition, the reaction mixture is allowed to warm to ambient temperature where it is stirred for about 18 hours. After this time the reaction mixture is cooled in an ice-water bath, and the reaction is quenched with the careful dropwise addition of water. Upon completion of addition, the reaction mixture is made basic with the slow addition of aqueous 10% sodium hydroxide. The mixture is then made acidic with aqueous 2N hydrochloric acid. The organic layer is separated and dried with magnesium sulfate. The mixture is filtered and concentrated under reduced pressure, yielding 41.7 grams of 2-methyl-2-(4-chlorophenyl)propanol. The NMR spectrum is consistent with the proposed structure.

Step B Synthesis of 2-methyl-2-(4-chlorophenyl) propanaldehyde as an intermediate To a stirring solution of 41.7 grams (0.226 mole) of 2-methyl-2-(4-chlorophenyl)propanol in 100 mL of dimethyl sulfoxide is added 126 mL (0.904 mole) of triethylamine. A solution of 63.0 grams (0.452 mole) of triethylamine-sulfur trioxide complex in 300 mL of dimethyl sulfoxide is then added portionwise during a 15 minute period. Upon completion of addition, the reaction mixture is stirred at ambient temperature for about five hours. The reaction mixture is then poured into about 500 mL of ice, and made acidic with aqueous 2N hydrochloric acid. The mixture is then extracted with two 100 mL portions of diethyl ether. The combined extracts are dried with magnesium sulfate and filtered. The filtrate is concentrated under reduced pressure, yielding 22.9 grams of 2-methyl-2-(4-chlorophenyl)propanaldehyde. The NMR spectrum is consistent with the proposed structure.

Step C Synthesis of 3-methyl-3-(4-chlorophenyl)-1-iodo-1-butene as an intermediate, This compound is prepared in a manner analogous to that of Step C, of Example 4, using 5.0 grams (0.027 mole) of 2-methyl-2-(4-chlorophenyl)propanaldehyde, 21.6 grams (0.054 mole) of iodoform, and 20.2 grams (0.162 mole) of chromium(II) chloride in 200 mL of tetrahydrofuran. The yield of 3-methyl-3-(4-chlorophenyl)-1-iodo-1-butene is 4.8 grams. The NMR spectrum is consistent with the proposed structure.

Step D Synthesis of 3-methyl-3-(4-chlorophenyl)-1-trimethylstannyl-1-butene as an intermediate A stirring solution of 4.8 grams (0.016 mole) of 3-methyl-3-(4-chlorophenyl)-1-iodo-1-butene in 50 mL of tetrahydrofuran is cooled to about −90° C., and 6.9 mL (0.018 mole) of n-butyllithium (2.5M in hexane) is added dropwise at a rate to maintain the reaction mixture temperature at about −85° to −90° C. Upon completion of the addition, the reaction mixture is stirred at −90° C. for 30 minutes. After this time, a solution of 3.7 grams (0.019 mole) of trimethyltin chloride in 10 mL of tetrahydrofuran is added dropwise at a rate sufficient to maintain the reaction mixture temperature at about −85° to −90° C. Upon completion of addition, the reaction mixture is again stirred at −90° C. for 30 minutes. After this time, the reaction mixture is allowed to warm to ambient temperature where it is stirred for about 18 hours. The reaction mixture is then poured into 150 mL of water and extracted with 150 mL of diethyl ether. The ether extract is dried with magnesium sulfate and filtered. The filtrate is concentrated under reduced pressure, yielding 4.8 grams of 3-methyl-3-(4-chlorophenyl)-1-trimethylstannyl-1-butene. The NMR spectrum is consistent with the proposed structure.

Step E Synthesis of 2,4-diamino-6-methyl-5-[3-(4-chlorophenyl)-3-methyl-1-butenyl]pyrimidine (Compound 21)

This compound is prepared in a manner analogous to that of Step E of Example 6, using 4.8 grams (0.014 mole) of 3-methyl-3-(4-chlorophenyl)-1-trimethylstannyl-1-butene, 2.7 grams (0.011 mole) of 2,4-diamino-5-iodo-6-methylpyrimidine (prepared in Step B of Example 3), 2.8 grams (0.066 mole) of lithium chloride, 0.4 gram (5 mole %) of bis(triphenylphosphine)palladium(II) chloride, and about 0.05 gram catalyst) of 2,6-di-tert-butyl-4-methylphenol in 25 mL of N,N-dimethylformamide. After heating at 65° C. for about 2.5 days, the reaction mixture is cooled and diluted with 100 mL of N,N-dimethylformamide. The mixture is filtered, and the filtrate is poured into 300 mL of water. The mixture then is extracted with two 200 mL portions of ethyl acetate. The combined extracts are dried with magnesium sulfate and filtered. The filtrate is concentrated under reduced pressure to a residue. The residue is adsorbed onto silica gel and subjected to column chromatography, using 10% methanol in methylene chloride as the eluant. The product-containing fractions are combined and concentrated under reduced pressure to a residue. NMR analysis of the residue indicates that it is impure product. The residue is subjected to column chromatography on basic alumina (activity II), using 2%, 4%, and 6% methanol in methylene chloride as eluants. The product-containing fractions are combined and concentrated Under reduced pressure, yielding about 2.0 grams of 2,4-diamino-6-methyl-5-[3-(4-chlorophenyl)-3-methyl-1-butenyl]pyrimidine, mp 195°–200° C. The NMR spectrum is consistent with the proposed structure.

Example 15

SYNTHESIS OF 2,4-DIAMINO-6-METHYL-5-[3-(4-CHLOROPHENYL)-3-METHYL-1-BUTYNYL] PYRIMIDINE (COMPOUND 43)

Step A Synthesis of 3-(4-chlorophenyl)-3-methyl-1-tributylstannylbutanol as an intermediate This compound is prepared in a manner, analogous to that of Step B of Example 6, using 5.0 mL (0.036 mole) of diisopropylamine, 4.3 mL (0.036 mole) of n-butyllithium (2.5M in hexanes), 9.6 grams (0.036 mole) of tri-butyltin hydride and 7.0 grams (0.036 mole) of 3-(4-chlorophenyl)-3-methylbutraldehyde (prepared as in Step A of Example 13) in 110 mL of tetrahydrofuran. The yield of 3-(4-chlorophenyl)-3-methyl-1-tributylstannylbutanol is 17.4 grams. The NMR spectrum is consistent with the proposed structure.

Step B Synthesis of 3-(4-chlorophenyl)-3-methyl-1-iodo-1-tributylstannylbutane as an intermediate This compound is prepared in a manner analogous to that of Step C of Example 6, using 14.0 grams (0.053 mole) of triphenylphosphine, 3.6 grams (0.053 mole) of imidazole, 13.6 grams (0.053 mole) iodine, and 17.4 grams (0.036 mole) of 3-(4-chlorophenyl)-3-methyl-1-tributylstannylbutanol in about 90 mL of methylene chloride. The yield of 3-(4-chlorophenyl)-3-methyl-1-iodo-71-tributylstannylbutane is 8.7 grams. The NMR spectrum is consistent with the proposed structure.

Step C Synthesis of 3-(4-chlorophenyl)-3-methyl-1-tributylstannyl-1-butene as an intermediate This compound is prepared in a manner analogous to that of Step D of Example 6, using 8.7 grams (0.015 mole) of 3-(4-chlorophenyl)-3-methyl-1-iodo-1-tributylstannylbutane and 6.5 mL (0.045 mole) of 1,8-diazabicyclo[5.4.0]undec-7-ene (DBU) in 50 mL of tetrahydrofuran. The yield of 3-(4-chlorophenyl)-3-methyl-1-tributylstannyl-1-butene is 5.3 grams. The NMR spectrum is consistent with the proposed structure.

Step D Synthesis of 3-(4-chlorophenyl)-3-methyl-1-butyne as an intermediate

A mixture of 4.0 grams (0.0085 mole) of 3-(4-chlorophenyl)-3-methyl-1-tributylstannyl-1-butene and 4.3 grams (0.0096 mole) of lead tetraacetate in 30 mL of anhydrous acetic anhydride is stirred at ambient temperature for about 18 hours. After this time, the reaction mixture is diluted to 100 mL with pentane. The mixture was then filtered through a pad of diatomaceous earth. The pad of diatomaceous earth is washed with about 300 mL of pentane. The wash and the filtrate are combined and concentrated under reduced pressure to a residue. The residue is subjected to column chromatography on silica gel, using petroleum ether as the eluant. The product-containing fractions are combined and concentrated under reduced pressure, yielding about 1.1 grams of 3-(4-chlorophenyl)-3-methyl-1-butyne. The NMR spectrum is consistent with the proposed structure.

Step E Synthesis of 2,4-diamino-6-methyl-5-[3-(4-chlorophenyl)-3-methyl-1-butynyl]pyrimidine (Compound 43)

This compound is prepared in a manner analogous to that of Step C of Example 3, using 0.8 gram (0.0032 mole) of 2,4-diamino-5-iodo-6-methylpyrimidine, 0.7 gram of (0.0040 mole) of 3-(4-chlorophenyl)-3-methyl-1-butyne, 0.3 gram of bis(triphenylphosphine)palladium(II) chloride, 0.03 gram of copper iodide, and 10 mL of piperidine; yielding 0.8 gram of 2,4-diamino-6-methyl-5-[[3-(4-chlorophenyl)-3-methyl-1-butynyl]pyrimidine, mp 188°–190° C. (Compound 43) The NMR spectrum is consistent with the proposed structure.

In an analogous manner there may also be obtained the corresponding 2,4-diamino-6-methyl-5-[2-[1-(4-chlorophenyl)-1-cyclopentyl]ethynyl]pyrimidine, mp 159°–161° C. (Compound 106).

Example 16

SYNTHESIS OF 2,4-DIAMINO-6-METHYL-5-[2-[2-(4-CHLOROPHENYL)-2-(1,3-DIOXOLANYL)] ETHYNYL]PYRIMIDINE (COMPOUND 108)

A stirring solution of 2.9 grams (0.01 mole) of 2,4-diamino-6-methyl-5-[3-(4-chlorophenyl)-3-oxo-1-propynyl]pyrimidine (Compound 46—prepared as in Example 9), 12.4 grams (0.20 mole) of ethylene glycol, and 0.1 gram (0.0001 mole—catalyst) of 1-hydroxy-3-(isothiocyanato)tetrabutyldistannoxane (prepared by the method of J. Otera et al., JOC, (1991), 56, 5307–5311) in 500 mL of toluene is heated at reflux for about 27 hours. After this time, the reaction mixture is cooled and concentrated under reduced pressure to a residue. The residue is purified by column chromatography on silica gel, yielding 2,4-diamino-6-methyl-5-[2-[2-(4-chlorophenyl)-2-(1,3-dioxolanyl)]ethynyl]pyrimidine.

NOTE: The procedure to prepare 2,4-diamino-6-methyl-5-[2-[2-(4-chlorophenyl)-2-(1,3-dioxolanyl)]ethynyl] pyrimidine as shown above is disclosed by J. Otera et al., Tetrahedron, (1992), 48, No. 8, 1449–1456.

Example 17

SYNTHESIS OF TRANS-2,4-DIAMINO-6-METHYL-5-[3-(4-TRIFLUOROMETHYLPHENYL)-3-METHYL-1-BUTENYL]PYRIMIDINE (COMPOUND 68)

Step A Synthesis of 4-trifluoromethylphenylacetonitrile as an intermediate

A stirred solution of 250.0 grams (1.05 moles) of 4-trifluoromethylphenylmethyl bromide in 1000 mL of ethanol was heated to about 80° C., and a solution of 109.0 grams (1.67 moles) of potassium cyanide in about 275 mL of water was added. Upon completion of addition, the reaction mixture Was stirred at 80° C. for about 1.75 hours. After this time the reaction mixture was cooled to ambient temperature and extracted with three portions of diethyl ether. The combined extracts were washed with two portions of water and one portion of an aqueous solution saturated with sodium chloride. The organic layer was added with magnesium sulfate and filtered. The filtrate was concentrated under reduced pressure, yielding about 197 grams of 4-trifluoromethylphenylacetonitrile.

Step B Synthesis of 2-methyl-2-(4-trifluoromethylphenyl) propanenitrile as an intermediate A stirred solution of 101.3 grams (0.55 mole) of 4-trifluoromethylphenylacetonitrile in 300 mL of tetrahydrofuran was cooled in an ice-bath, and a solution of 194.1 grams (1.37 moles) of iodomethane in 100 mL of tetrahydrofuran was added. Upon completion of addition, a solution of 153.5 grams (1.37 moles) of potassium tert.-butoxide in 900 mL of tetrahydrofuran was then added dropwise. Upon completion of addition, the reaction mixture was stirred at ambient temperature for about 18 hours. The reaction mixture was stirred with about 400 mL of water, then aqueous 1N hydrochloric acid was added until the color of the reaction mixture changed from red to yellow. Water was then added to the reaction mixture to cause an oily residue to separate from the mixture. The water was decanted from the oil, and the oil was dissolved in diethyl ether. The ether solution was washed with two portions of water and two portions of an aqueous solution saturated with sodium chloride. The ether solution was then. dried with magnesium sulfate and filtered. The filtrate was concentrated under reduced pressure, yielding about 119.8 grams of 2-methyl-2-(4-trifluoromethylphenyl)propanenitrile. The NMR spectrum was consistent with the proposed structure.

Step C Synthesis of 2-methyl-2-(4-trifluoromethylphenyl) propanaldehyde as an intermediate A stirred solution of 119.8 grams (0.56 mole) of 2-methyl-2-(4-trifluoromethylphenyl)propanenitrile in 100 mL of toluene was cooled to −50° C., and 487 mL (0.73 mole) of diisobutylaluminium hydride (1.5M in toluene) was added dropwise during a 45 minute period while keeping the reaction mixture temperature between –45° and –50° C. Upon completion of addition, the reaction mixture was stirred at –50° C. for 30 minutes. The reaction mixture was then warmed to about 0° C., where it stirred for an additional 30 minutes. After this time, the reaction mixture was carefully poured into 1000 mL of ice-cold aqueous 1.5M sulfuric acid. The resultant mixture was stirred for about three hours, then it was allowed to stand for about 18 hours. The aqueous layer was separated and extracted with 200 mL of diethyl ether. The organic layer and the diethyl ether extract were combined and dried with magnesium sulfate. The mixture was filtered, and the filtrate was concentrated under reduced pressure, yielding 102.3 grams of 2-methyl-2-(4-trifluoromethylphenyl)propanaldehyde. The NMR spectrum was consistent with the proposed structure.

Step D Synthesis of bromomethyl triphenylphosphonium bromide as an intermediate

Under a nitrogen atmosphere, a stirred solution of 215.0 grams (0.82 mole) of triphenylphosphine and 115 mL (1.64 moles) of dibromomethane in 600 mL of toluene was heated at reflux for about eight hours. After this time a solid was collected by filtration. The filtrate was again heated to reflux where it stirred for an additional eight hours. The mixture was cooled and additional solid was collected by filtration. The two solids were combined, yielding about 280 grams of bromomethyl triphenylphosphonium bromide.

Step E Synthesis of cis/trans -1-bromo-3-methyl-3-(4-trifluoromethylphenyl)-1-butene as an intermediate Under a nitrogen atmosphere, a stirred solution of 101.0 grams (0.23 mole) of bromomethyl triphenylphosphonium bromide in 400 mL of tetrahydrofuran was cooled in a dry ice-acetone bath, and 26.0 grams (0.23 mole) of potassium tert.-butoxide was added portionwise while maintaining the reaction mixture temperature between –70° and –75° C. Upon completion of addition, the reaction mixture was stirred at –75° C. for about 90 minutes. After this time a solution of 50.0 grams (0.23 mole) of 2-methyl-2-(4-trifluoromethylphenyl)propanaldehyde (prepared in Step C of this Example) in 100 mL of tetrahydrofuran was added dropwise while maintaining the reaction mixture temperature below –65° C. Upon completion of addition, the reaction mixture was allowed to warm to ambient temperature as it stirred for about 18 hours. The reaction mixture was then poured into 500 mL of water and extracted with two 300 mL portions of diethyl ether. The combined extracts were dried with magnesium sulfate and filtered. The filtrate was concentrated under reduced pressure to a residual oil. The oil was subjected to column chromatography on silica gel using petroleum ether as the eluant. The product-containing fractions were combined and concentrated under reduced pressure, yielding 40.9 grams of cis/trans-1-bromo-3-methyl-3-(4-trifluoromethylphenyl)-1-butene. The NMR spectrum was consistent with the proposed structure.

Step F Synthesis of 3-methyl-3-(4-trifluoromethylphenyl)-1-butyne as an intermediate Under a nitrogen atmosphere, a stirred solution of 40.9 grams (0.14 mole) of cis/trans-1-bromo-3-methyl-3-(4-trifluoromethylphenyl)-1-butene and 47.0 grams (0.42 mole) of potassium tert.-butoxide in 300 mL of tert.-butanol was heated at reflux for about three hours. After this time the reaction mixture was allowed to cool to ambient temperature as it stirred for about 18 hours. The reaction mixture was then poured into 300 mL of water and extracted with one 200 mL portion of diethyl ether. The extract was dried with magnesium sulfate, filtered, and concentrated under reduced pressure to a residue. The residue was subjected to column chromatography on silica gel using petroleum ether as the eluant. The product-containing fractions were combined and concentrated under reduced pressure, yielding 25.2 grams of 3-methyl-3-(4-trifluoromethylphenyl)-1-butyne. The NMR spectrum was consistent with the proposed structure.

Step G Synthesis of trans-3-methyl-3-(4-trifluoromethylphenyl)-1-butenylboronic acid as an intermediate Under a nitrogen atmosphere, a stirred mixture of 25.2 grams (0.12 mole) of 3-methyl-3-(4-trifluoromethylphenyl)-1-butyne and 12.7 mL (0.12 mole) of 1,3,2-benzodioxaborole was warmed to 70° C. where it stirred for six hours. The reaction mixture was then cooled and poured slowly into 500 mL of ice-water while flushing with nitrogen. The mixture was then allowed to warm to ambient temperature where it stirred for about 18 hours. The mixture was cooled in an ice-bath, and the resultant solid was collected by filtration. The solid was washed with water and then dissolved in diethyl ether. The solution was washed with 100 mL of an aqueous solution saturated with sodium chloride. The organic layer was dried with magnesium sulfate, filtered, and concentrated under reduced pressure to a residual solid. The solid was dried under vacuum without heat, yielding 27.6 grams of trans-3-methyl-3-(4-trifluoromethylphenyl)-1-butenylboronic acid.

NOTE: The procedure to prepare trans-3-methyl-3-(4-trifluoromethylphenyl)-1-butenylboronic acid as shown above is disclosed in two references by G. W. Kabalka et al., Synthetic Communications, 11(3), 247–251 (1981) and Synthetic Communications, 13(12), 1027–1032 (1983).

Step H Synthesis of trans-2,4-diamino-6-methyl-5-[3-(4-trifluoromethylphenyl)-3-methyl-1-butenyl]pyrimidine (Compound 68)

Sodium metal, 4.1 grams (0.18 mole), was stirred with 250 mL of ethanol for 30 minutes. After this time 20.0 grams (0.08 mole) of 2,4-diamino-5-iodo-6-methylpyrimidine (prepared in Step B of Example 3), 27.6 grams (0.11 mole) of trans-3-methyl-3-(4-trifluoromethylphenyl)-1-butenylboronic acid, and 9.2 grams (0.008 mole) of tetrakistriphenylphosphine palladium(0) were added. The reaction miXture was purged with nitrogen, and then heated to 80° C. where it stirred for about 28 hours. After this time the reaction mixture was concentrated under reduced pressure to about 20% of the original volume and then poured into 300 mL of water. The mixture was cooled in an ice-bath, and a solid was collected by filtration. The solid was triturated with a mixture of 1:1 petroleum ether:diethyl ether, and then subjected to column chromatography on silica gel using 5% methanol in methylene chloride as the eluant. The product-containing fractions were combined and concentrated under reduced pressure to a solid residue. The solid was recrystallized from 1-propanol and water, yielding 15.2 grams of trans-2,4-diamino-6-methyl-5-[3-(4-trifluoromethylphenyl)-3-methyl-1-butenyl]pyrimidine, mpt 82°–185° C. The NMR spectrum was consistent with the proposed structure.

Example 18

SYNTHESIS OF 2,4-DIAMINO-6-METHYL-5-[3-(4-TRIFLUOROMETHYLPHENYL)-3-METHYL-1-BUTYNYL]PYRIMIDINE (COMPOUND 84)

This compound was prepared in a manner analogous to that of Step C of Example 3, using 1.3 grams (0.005 mole) of 2,4-diamino-5-iodo-6-methylpyrimidine, 1.6 grams of (0.008 mole) of 3-methyl-3-(4-trifluoromethylphenyl)-1-butyne (prepared as in Step F of Example 17), 0.3 gram of bis(triphenylphosphine)palladium(II) chloride, 0.05 gram of copper iodide, and 8 mL of piperidine in 20 mL of N,N-dimethylformamide, yielding 1.6 grams of 2,4-diamino-6-methyl-5-[3-(4-trifluoromethylphenyl)-3-methyl-1-butynyl]pyrimidine, mp 153°–157° C. The NMR spectrum is consistent with the proposed structure.

Example 19

SYNTHESIS OF TRANS-2-AMINO-4-PROPYLAMINO-6-METHYL-5-[3-(4-TRIFLUOROMETHYLPHENYL)-3-METHYL-1-BUTENYL]PYRIMIDINE (COMPOUND 140)

Step A Synthesis of 2-amino-4-propylamino-6-methylpyrimidine as an intermediate

Under a nitrogen atmosphere, a solution of 17.0 grams (0.12 mole) of 2-amino-4-chloro-6-methylpyrimidine (commercially available) and 20 mL (0.24 mole) of n-propylamine was stirred, and 25 mL of ethanol was added. Upon completion of addition, the reaction mixture was stirred at ambient temperature for one hour. After, this time, the reaction mixture was heated to reflux where it stirred for 2.5 hours. An additional five mL of n-propylamine was added to the reaction mixture, then it was allowed to stir at ambient temperature for about 18 hours. The reaction mixture was concentrated under reduced pressure, and the residue was dissolved in 250 mL of 10% methanol in methylene chloride. The cloudy solution was filtered through 300 grams of basic alumina (deactivated with 18 mL of water) using 10% methanol in methylene chloride as the eluant. The product-containing fractions were combined and concentrated under reduced pressure, yielding about 21 grams of 2-amino-4-propylamino-6-methylpyrimidine. The NMR spectrum was consistent with the proposed structure.

Step B Synthesis of 2-amino-4-propylamino-5-iodo-6-methylpyrimidine as an intermediate Under a nitrogen atmosphere, a solution of 20.0 grams (0.12 mole) of 2-amino-4-propylamino-6-methylpyrimidine in 100 mL of acetic acid was stirred, and a mixture of 25.8 grams (0.16 mole) of iodine monochloride in 25 mL of acetic acid was added rapidly during a five minute period. Upon completion of addition, the reaction mixture was stirred at ambient temperature for about 18 hours. After this time about 15 grams of sodium acetate was added to the reaction mixture, which was then concentrated under reduced pressure to about one-half volume. The reaction mixture was then diluted with 100 mL of water and 200 mL of ethyl acetate. The mixture was then cooled and made strongly basic with 100 mL of 50% aqueous sodium hydroxide. The aqueous layer was separated and extracted with three 100 mL portions of ethyl acetate. The extracts were combined with the organic layer, and the combination was washed with one 100 mL portion of water and one 100 mL portion of an aqueous solution saturated with sodium chloride. The organic layer was dried with magnesium sulfate and filtered. The filtrate was concentrated under reduced pressure at 50° C., yielding 33.3 grams of oil. The oil was dried under vacuum for six hours at 60° C., yielding 32.4 grams of solid 2-amino-4-propylamino-5-iodo-6-methylpyrimidine. The NMR spectrum was consistent with the proposed structure.

Step C Synthesis of trans-2-amino-4-propylamino-6-methyl-5-[3-(4-trifluoromethylphenyl)-3-methyl-1-butenyl]pyrimidine (Compound 140)

This compound was prepared in a manner analogous to that of Step H of Example 17, using 2.1 grams (0.007 mole) of 2-amino-4-propylamino-5-iodo-6-methylpyrimidine, 2.1 grams (0.008 mole) of trans-3-methyl-3-(4-trifluoromethylphenyl)-1-butenylboronic acid, 0.3 gram (catalyst) of tetrakistriphenylphosphine palladium(0), 0.4 gram (0.019 mole) of sodium metal in 40 mL of ethanol. This preparation differed from that of Step H of Example 17 in that an antioxidant, about 0.1 gram of 2,6-di-tert.-butyl-4-methylphenol, was used. The yield of trans-2-amino-4-propylamino-6-methyl-5-[3-(4-trifluoromethylphenyl)-3-methyl-1-butenyl]pyrimidine was 2.0 grams, mp 140°–141° C. The NMR spectrum was consistent with the proposed structure.

Example 20

SYNTHESIS OF TRANS-2-(1-METHYLETHYLCARBONYL)AMINO-4-(PROPYLAMINO)-6-METHYL-5-[3-(4-CHLOROPHENYL)-1-BUTENYL]PYRIMIDINE (COMPOUND 143)

This compound is prepared in a manner analogous to that of Example 8, using 0.38 gram (0.001 mole) trans-2-amino-4-propylamino-6-methyl-5-[3-(4-trifluoromethylphenyl)-3-methyl-1-butenyl]pyrimidine (Compound 140—prepared in Example 19) and 0.01 gram (catalyst) of 4-dimethylaminopyridine in 5 mL of isobutyric anhydride, yielding trans-2-(1-methylethylcarbonyl)amino-4-(propylamino)-6-methyl-5-[3-(4-chlorophenyl)-1-butenyl]pyrimidine.

Example 21

SYNTHESIS OF TRANS-2,4-DIAMINO-6-METHYL-5-[3-(2,6-DI-t-BUTYL-4-PYRIDYL)-3-METHYL-1-BUTENYL]PYRIMIDINE (COMPOUND 198)

In accordance with the procedures of Example 17, but starting with 4-bromomethyl-2,6-di-t-butylpyrimidine in place of 4-trifluoromethylphenylmethyl bromide, there was obtained the corresponding 3-(2,6-di-t-butyl-4-pyridyl)-1-butenyl compound (Compound 198). The NMR spectrum was consistent with the proposed structure; m.p., 214°–216° C.

Example 22

SYNTHESIS OF 2,4-DIAMINO-6-METHYL-5-[3-(2,6-DI-t-BUTYL-4-PYRIDYL)-3-METHYL-1-BUTYNYL]PYRIMIDINE (COMPOUND 201)

In accordance with the procedures of Example 21, but using the 2,6-di-t-butylpyridyl-1-butyne (prepared analogous to the product of Step F of Example 17) instead of the 1-butenyl intermediate, there was obtained the corresponding 3-(2,6-di-t-butyl-4-pyridyl)-1-butynyl compound (Compound 201). The NMR spectrum was consistent with the proposed structure; m.p., 160°–162° C.

TABLE 1

Pesticidal 5-[ω-(Substituted aryl)-alkenylene and alkynylene]-2,4-diaminopyrimidines where R, $R^1$, $R^2$, $R^3$ are hydrogen, and $R^4$ is $-CH_3$;

| Cmpd. No. | U | V | W | X | Y | Z |
|---|---|---|---|---|---|---|
| 1 | $-CH=CHCH_2-$ | H | H | Cl | H | H |
| 2 | $-CH=CHCH_2-$ | Cl | H | Cl | H | H |
| 3 | $-CH=CHCH_2-$ | Cl | H | H | H | Cl |
| 4 | $-CH=CHCF_2-$ | H | H | Cl | H | H |
| 5 | $-CH=CHCH(CH_3)-$ | Cl | H | H | H | H |
| 6 | $-CH=CHCH(CH_3)-$ | H | Cl | H | H | H |
| 7 | $-CH=CHCH(CH_3)-$ trans isomer | H | H | Cl | H | H |
| 8 | $-CH=CHCH(CH_3)-$ | H | H | F | H | H |
| 9 | $-CH=CHCH(CH_3)-$ | Cl | H | Cl | H | H |
| 10 | $-CH=CHCH(CH_3)-$ | H | Cl | Cl | H | H |
| 11 | $-CH=CHCH(CH_3)-$ | H | Cl | H | Cl | H |
| 12 | $-CH=CHCH(CH_3)-$ | H | H | $-CH_3$ | H | H |
| 13 | $-CH=CHCH(CH_3)-$ | H | $-CF_3$ | H | H | H |
| 14 | $-CH=CHCH(CH_3)-$ | H | H | $-CF_3$ | H | H |
| 15 | $-CH=CHCH(CH_3)-$ | H | H | $-OC_4H_9$ | H | H |
| 16 | $-CH=CHCH(CH_3)-$ | H | H | $-OCF_3$ | H | H |
| 17 | $-CH=CHCH(CH_3)-$ | H | H | $-CH_2OCH_3$ | H | H |
| 18 | $-CH=CHCH(CH_3)-$ | H | H | $-SO_2CH_3$ | H | H |
| 19 | $-CH=CHCH(CH_3)-$ | H | H | 4-F-phenyl | H | H |
| 20 | $-CH=CHCH(OCH_3)-$ | H | H | Cl | H | H |
| 21 | $-CH=CHC(CH_3)_2-$ | H | H | Cl | H | H |
| 22 | (propenyl-methylcyclopropyl) | H | H | Cl | H | H |
| 23 | (propenyl-methylcyclobutyl) | H | H | Cl | H | H |
| 24 | (propenyl-methylcyclopentyl) | H | H | Cl | H | H |
| 25 | (propenyl-methylcyclohexyl) | H | H | Cl | H | H |
| 26 | $-CH=CHSi(CH_3)_2-$ | H | H | Cl | H | H |
| 27 | $-CH=CH-C(O)-CH_2-$ | H | H | Cl | H | H |
| 28 | $-CH=CHC(CH_3)_2CH_2-$ | H | H | Cl | H | H |
| 29 | $-CH=CHCH_2C(CH_3)_2-$ | H | H | Cl | H | H |
| 30 | $-CH_2CH=CH-$ | H | H | H | H | H |
| 31 | $-CH_2CH=CH-$ | Cl | H | Cl | H | Cl |
| 32 | $-C_2H_4CH=CH-$ | H | H | H | H | H |
| 33 | $-CH_2CH=C(CH_3)-$ trans isomer | H | H | H | H | H |
| 34 | $-CH_2CH=C(CH_3)-$ | H | H | Cl | H | H |

TABLE 1-continued

Pesticidal 5-[ω-(Substituted aryl)-alkenylene and alkynylene]-2,4-diaminopyrimidines

| Cmpd No. | | V | W | Y | Z | |
|---|---|---|---|---|---|---|
| 35 | —CH₂CH=C(CH₃)— | Cl | H | H | Cl | H |
| 36 | —CH₂CH=C(CH₃)— trans isomer | H | Cl | Cl | H | H |
| 37 | —CH₂CH=C(CH₃)— trans isomer | H | H | —CH₃ | H | H |
| 38 | —CH₂CH=C(CH₃)— trans isomer | H | H | —CF₃ | H | H |
| 39 | —C≡CCH₂— | H | H | H | H | H |
| 40 | —C≡CCH₂— | H | H | Cl | H | H |
| 41 | —C≡CCH(CH₃)— | H | H | Cl | H | H |
| 42 | —C≡CCH(OCH₃)— | H | H | Cl | H | H |
| 43 | —C≡CC(CH₃)₂— | H | H | Cl | H | H |
| 44 | 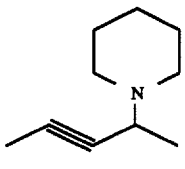 | H | H | Cl | H | H |
| 45 | —C≡CSi(CH₃)₂— | H | H | Cl | H | H |
| 46 | 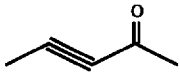 | H | H | Cl | H | H | where $R^3$ is hydrogen, $R^4$ is —CH₃, U is —CH=CHCH(CH₃)—; V, W, Y, and Z are hydrogen; and X is chloro;

| Cmpd. No. | R | R¹ | R² |
|---|---|---|---|
| 47 | H | —C₂H₅ | H |
| 48 | H | 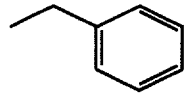 | H |
| 49 | H | —CH₃ | —CH₃ |
| 50 | H | —CH₂CH₂CH₂CH₂CH₂— | |
| 51 | 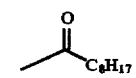 | —CH₃ | —CH₃ |
| 52 | 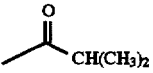 | —CH₂CH₂OCH₂CH₂— | |
| 53 | 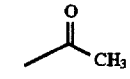 | H | 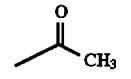 |
| 54 | 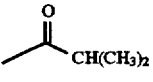 | H | 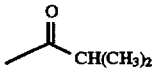 |
| 55 | 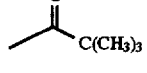 | H | 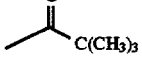 |
| 56 | 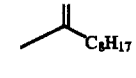 | H | 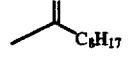 |
| 57 | 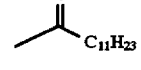 | H | 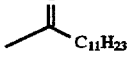 |

TABLE 1-continued

Pesticidal 5-[ω-(Substituted aryl)-alkenylene and alkynylene]-2,4-diaminopyrimidines

| 58 | 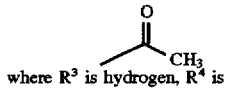 | —C₂H₅ | H | where R³ is hydrogen, R⁴ is —CH₃, U is —CF=CHCH(CH₃)₂—; V, W, Y, and Z are hydrogen; and X is chloro;

| 59 | 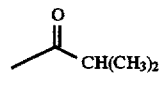 | H | 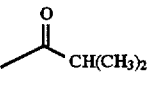 | where R³ is hydrogen, R⁴ is —CH₃, U is —CF=CHCH(CH₃)—; V, W, Y, and Z are hydrogen; and X is chloro;

| 60 | 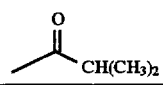 | H | 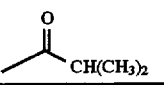 | where R, R¹, R², and R³ are hydrogen, and R⁴ is —CH₃;

| Cmpd. No. | U | V | W | X | Y | Z |
|---|---|---|---|---|---|---|
| 61 | —CF=CHCH(CH₃)— | H | H | Cl | H | H |
| 62 | —CF=CHC(CH₃)₂— | H | H | Cl | H | H |
| 63 | —CH₂CH=CH— trans isomer | H | H | Cl | H | H |
| 64 | —CH₂CH=CH— cis/trans isomers | H | H | Cl | H | H |
| 65 | —C≡CCH(CH₃)— | H | H | H | H | H |
| 66 | —CH=CHC(CH₃)₂— trans isomer | H | H | F | H | H |
| 67 | —CH=CHC(CH₃)₂— | H | H | H | H | H |
| 68 | —CH=CHC(CH₃)₂— | H | H | —CF₃ | H | H |
| 69 | —CH=CHC(CH₃)₂— | H | H | —CH₂OCH₃ | H | H |
| 70 | —CH=CHC(CH₃)₂— | H | H | —CH₃ | H | H |
| 71 | —CH=CHC(CH₃)₂— | H | H | 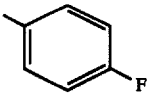 | H | H |
| 72 | —CH=CHC(CH₃)₂— | H | H | —OCF₃ | H | H |
| 73 | —CH=CHC(CH₃)₂— | H | H | —OC₄H₉ | H | H |
| 74 | —CH=CHC(CH₃)₂— | H | H | —SO₂CH₃ | H | H |
| 75 | —CH=CHC(CH₃)₂— | H | H | 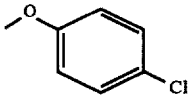 | H | H |
| 76 | —CH=CHC(CH₃)₂— | Cl | H | H | H | H |
| 77 | —CH=CHC(CH₃)₂— | H | Cl | H | H | H |
| 78 | —CH=CHC(CH₃)₂— | H | Cl | Cl | H | H |
| 79 | —CH=CHC(CH₃)₂— | Cl | H | Cl | H | H |
| 80 | —CH=CHC(CH₃)₂— | H | Cl | H | Cl | H |
| 81 | —CH=CHC(CH₃)₂— | —CF₃ | H | H | H | H |
| 82 | —CH=CHC(CH₃)₂— | H | —CF₃ | H | H | H |
| 83 | —C≡CC(CH₃)₂— | H | H | F | H | H |
| 84 | —C≡CC(CH₃)₂— | H | H | —CF₃ | H | H |
| 85 | —C≡CC(CH₃)₂— | H | H | —CH₂OCH₃ | H | H |
| 86 | —C≡CC(CH₃)₂— | H | H | —CH₃ | H | H |
| 86 | —C≡CC(CH₃)₂— | H | H | 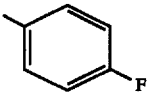 | H | H |
| 88 | —C≡CC(CH₃)₂— | H | H | —OCF₃ | H | H |
| 89 | —C≡CC(CH₃)₂— | H | H | —OC₄H₉ | H | H |
| 90 | —C≡CC(CH₃)₂— | H | H | —SO₂CH₃ | H | H |

TABLE 1-continued
Pesticidal 5-[ω-(Substituted aryl)-alkenylene and alkynylene]-2,4-diaminopyrimidines
| | | | | | | |
|---|---|---|---|---|---|---|
| 91 | —C≡CC(CH₃)₂— | H | H | 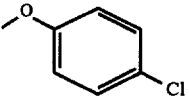 | H | H |
| 92 | —C≡CC(CH₃)₂— | Cl | H | H | H | H |
| 93 | —C≡CC(CH₃)₂— | H | Cl | H | H | H |
| 94 | —C≡CC(CH₃)₂— | H | Cl | Cl | H | H |
| 95 | —C≡CC(CH₃)₂— | Cl | H | Cl | H | H |
| 96 | —C≡CC(CH₃)₂— | H | Cl | H | Cl | H |
| 97 | —C≡CC(CH₃)₂— | —CF₃ | H | H | H | H |
| 98 | —C≡CC(CH₃)₂— | H | —CF₃ | H | H | H |
| 99 | —C≡CC(C₂H₅)₂— | H | H | Cl | H | H |
| 100 | —CH=CHC(C₂H₅)₂— | H | H | Cl | H | H |
| 101 | 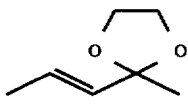 | H | H | Cl | H | H |
| 102 | 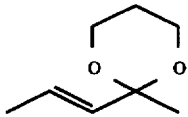 | H | H | Cl | H | H |
| 103 | 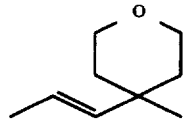 | H | H | Cl | H | H |
| 104 | 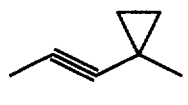 | H | H | Cl | H | H |
| 105 | 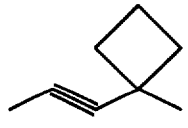 | H | H | Cl | H | H |
| 106 | 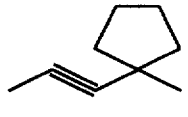 | H | H | Cl | H | H |
| 107 | 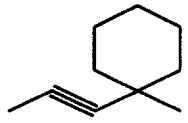 | H | H | Cl | H | H |
| 108 | 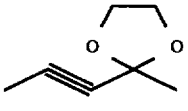 | H | H | Cl | H | H |
| 109 | 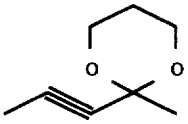 | H | H | Cl | H | H |

TABLE 1-continued

Pesticidal 5-[ω-(Substituted aryl)-alkenylene and alkynylene]-2,4-diaminopyrimidines

| 110 | [4-methyl-4-(1-propynyl)tetrahydropyran] | H | H | Cl | H | H | where $R^3$ is hydrogen, $R^4$ is $-CH_3$, U is $-CH=CHC(CH_3)_2-$; V, W, Y, and Z are hydrogen; and X is chloro;

| Cmpd. No. | R | $R^1$ | $R^2$ |
|---|---|---|---|
| 111 | $CH_3C(O)-$ | H | $CH_3C(O)-$ |
| 112 | $-C(O)CH_2OC_2H_5$ | H | $-C(O)CH_2OC_2H_5$ |
| 113 | $-C(O)OC_2H_5$ | H | $-C(O)OC_2H_5$ |
| 114 | $-C(O)C_2H_4OC_2H_5$ | H | $-C(O)C_2H_4OC_2H_5$ |
| 115 | $-C(O)C_2H_4OC_2H_4OC_2H_5$ | H | $-C(O)C_2H_4OC_2H_4OC_2H_5$ |
| 116 | $-C(O)C_5H_{11}$ | H | $-C(O)C_5H_{11}$ |
| 117 | $-C(O)CH(CH_3)_2$ | H | $-C(O)CH(CH_3)_2$ |
| 118 | $-C(O)-(3-pyridyl)$ | H | $-C(O)-(3-pyridyl)$ |
| 119 | $-C(O)-cyclohexyl$ | H | $-C(O)-cyclohexyl$ | where $R^3$ is hydrogen, $R^4$ is $CH_3$, U is $-C\equiv CC(CH_3)_2-$; V, W, Y, and Z are hydrogen; and X is chloro;

| 120 | $-C(O)CH_3$ | H | $-C(O)CH_3$ |
| 121 | $-C(O)CH_2OC_2H_5$ | H | $-C(O)CH_2OC_2H_5$ |
| 122 | $-C(O)OC_2H_5$ | H | $-C(O)OC_2H_5$ |
| 123 | $-C(O)C_2H_4OC_2H_5$ | H | $-C(O)C_2H_4OC_2H_5$ |

TABLE 1-continued

Pesticidal 5-[ω-(Substituted aryl)-alkenylene and alkynylene]-2,4-diaminopyrimidines

| | | | |
|---|---|---|---|
| 124 | ![structure]: CH₃C(O)-C₂H₄OC₂H₄OC₂H₅ | H | CH₃C(O)-C₂H₄OC₂H₄OC₂H₅ |
| 125 | CH₃C(O)-C₅H₁₁ | H | CH₃C(O)-C₅H₁₁ |
| 126 | CH₃C(O)-CH(CH₃)₂ | H | CH₃C(O)-CH(CH₃)₂ |
| 127 | CH₃C(O)-(3-pyridyl) | H | CH₃C(O)-(3-pyridyl) |
| 128 | CH₃C(O)-cyclohexyl | H | CH₃C(O)-cyclohexyl | where $R^3$ is hydrogen, $R^4$ is $-CH_3$, U is $-CH=CHC(CH_3)_2-$; V, W, Y, Z, and $R^1$ are hydrogen;

| Cmpd. No. | R | $R^2$ | X |
|---|---|---|---|
| 129 | $-C_2H_5$ | $-C_2H_5$ | Cl |
| 130 | $-CH(CH_3)_2$ | $-CH(CH_3)_2$ | $-CF_3$ | where $R^3$ is hydrogen, $R^4$ is $-CH_3$, U is $-C \equiv CC(CH_3)_2-$; V, W, Y, Z, and $R^1$ are hydrogen;

| 131 | $-C_3H_7$ | $-C_3H_7$ | Cl |
| 132 | $-CH(CH_3)_2$ | $-CH(CH_3)_2$ | $-CF_3$ | where R, $R^1$, $R^2$, and $R^3$ are hydrogen, and $R^4$ is $-CH_3$;

| Cmpd. No. | U | V | W | X | Y | Z |
|---|---|---|---|---|---|---|
| 133 | $-CH=CHCH_2-$ trans isomer | H | H | H | H | H |
| 134 | $-C \equiv CCH(CH_3)-$ | H | H | F | H | H |
| 135 | $-C \equiv CC(CH_3)_2-$ | H | H | H | H | H |
| 136 | $-C \equiv CC(CH_3)_2CH_2-$ | H | H | Cl | H | H |
| 137 | CH₃CH=CH-(1-methylcyclopropyl), trans isomer | H | H | $-CF_3$ | H | H |
| 138 | CH₃C≡C-(1-methylcyclopropyl) | H | H | F | H | H |
| 139 | CH₃C≡C-(1-methylcyclopropyl) | H | H | $-CF_3$ | H | H | where $R^4$ is $-CH_3$, U is $-CH=CHC(CH_3)_2-$; V, W, Y, and Z are hydrogen; and X is $-CF_3$;

| Cmpd. No. | $R^1$ | $R^2$ | $R^3$ | R |
|---|---|---|---|---|
| 140 | H | H | $-C_3H_7$ | H |
| 141 | H | H | $-CH(CH_3)_2$ | H |
| 142 | CH₃C(O)-CH(CH₃)₂ | H | H | CH₃C(O)-CH(CH₃)₂ |

TABLE 1-continued

Pesticidal 5-[ω-(Substituted aryl)-alkenylene and alkynylene]-2,4-diaminopyrimidines

| | | | | |
|---|---|---|---|---|
| 143 | O=C(CH(CH₃)₂)– | H | —C₃H₇ | H |
| 144 | O=C(CH(CH₃)₂)– | H | —CH(CH₃)₂ | H |
| 145 | H | —C₃H₇ | H | H |
| 146 | H | —CH(CH₃)₂ | H | H |
| 147 | H | —C₃H₇ | —C₃H₇ | H |
| 148 | H | —CH(CH₃)₂ | —C₃H₇ | H |
| 149 | H | —C₃H₇ | —CH(CH₃)₂ | H |
| 150 | O=C(CH(CH₃)₂)– | —C₃H₇ | —C₃H₇ | O=C(CH(CH₃)₂)– |
| 151 | H | —C₃H₇ | H | O=C(CH(CH₃)₂)– |
| 152 | H | —CH(CH₃)₂ | H | O=C(CH(CH₃)₂)– |
| 153 | H | H | —C₄H₉ | H |
| 154 | H | —C₄H₉ | H | H |
| 155 | H | —C₄H₉ | —C₄H₉ | H |
| 156 | H | —CH₂CH₂-C₆H₅ | —CH₂CH₂-C₆H₅ | H |
| 157 | H | n-C₈H₁₇ | H | H |
| 158 | H | H | n-C₈H₁₇ | H |
| 159 | H | n-C₈H₁₇ | H | O=C(CH₃)– |
| 160 | O=C(CH₃)– | H | n-C₈H₁₇ | H |
| 161 | H | —C₃H₆OC₂H₅ | —OC₃H₆OC₂H₅ | H |
| 162 | H | —C₂H₄OC₂H₄OC₂H₅ | —C₂H₄OC₂H₄OC₂H₅ | H | where R⁴ is CH₃, U is —C≡CC(CH₃)₂—; V, W, Y, and Z are hydrogen;
and X is CF₃;

| | | | | |
|---|---|---|---|---|
| 163 | H | H | —C₃H₇ | H |
| 164 | H | H | —CH(CH₃)₂ | H |
| 165 | O=C(CH(CH₃)₂)– | H | H | O=C(CH(CH₃)₂)– |
| 166 | O=C(CH(CH₃)₂)– | H | —C₃H₇ | H |
| 167 | O=C(CH(CH₃)₂)– | H | —CH(CH₃)₂ | H |
| 168 | H | —C₃H₇ | H | H |
| 169 | H | —CH(CH₃)₂ | H | H |
| 170 | H | —C₃H₇ | —C₃H₇ | H |
| 171 | H | —CH(CH₃)₂ | —C₃H₇ | H |
| 172 | H | —C₃H₇ | —CH(CH₃)₂ | H |
| 173 | O=C(CH(CH₃)₂)– | —C₃H₇ | —C₃H₇ | O=C(CH(CH₃)₂)– |

TABLE 1-continued

Pesticidal 5-[ω-(Substituted aryl)-alkenylene and alkynylene]-2,4-diaminopyrimidines

| | | | | |
|---|---|---|---|---|
| 174 | H | —C₃H₇ | H | ![ketone with CH(CH₃)₂] |
| 175 | H | —CH(CH₃)₂ | H | ![ketone with CH(CH₃)₂] |
| 176 | H | H | —C₄H₉ | H |
| 177 | H | —C₄H₉ | H | H |
| 178 | H | —C₄H₉ | —C₄H₉ | H |
| 179 | H | ethylphenyl | ethylphenyl | H |
| 180 | H | n-C₈H₁₇ | H | H |
| 181 | H | H | n-C₈H₁₇ | H |
| 182 | H | n-C₈H₁₇ | H | —C(O)CH₃ |
| 183 | —C(O)CH₃ | H | n-C₈H₁₇ | H |
| 184 | H | —C₃H₆OC₂H₅ | —C₃H₆OC₂H₅ | H |
| 185 | H | —C₂H₄OC₂H₄OC₂H₅ | —C₂H₄OC₂H₄OC₂H₅ | H | where R, R¹, R², and R³ are hydrogen, R⁴ is —CH₃

| Cmpd No. | U | V | W | X | Y | Z |
|---|---|---|---|---|---|---|
| 186 | —CH=CHC(CH₃)₂— | H | t-Bu[(1)] | H | t-Bu[(1)] | H |
| 187 | —CH=CHC(CH₃)₂— | H | t-Bu | OH | t-Bu | H |
| 188 | —CH=CHC(CH₃)₂— | H | t-Bu | OCH₃ | t-Bu | H |
| 189 | —C≡CC(CH₃)₂— | H | t-Bu | H | t-Bu | H |
| 190 | —C≡CC(CH₃)₂— | H | t-Bu | OH | t-Bu | H |
| 191 | —C≡CC(CH₃)₂— | H | t-Bu | OCH₃ | t-Bu | H |
| 192 | —C≡CC(OH)CH₃— | H | H | Cl | H | H |
| 193 | —C≡CC(OCH₃)CH₃— | H | H | Cl | H | H |
| 194 | —CH=CHC(OH)CH₃— | H | H | Cl | H | H |
| 195 | —CH=CHC(OCH₃)CH₃— | H | H | Cl | H | H |
| 196 | —CH=CHCH(CH(CH₃)₂)— | H | H | Cl | H | H |
| 197 | —C≡CCH(CH(CH₃)₂)— | H | H | Cl | H | H |

[(1)] t-Bu is tertiary butyl

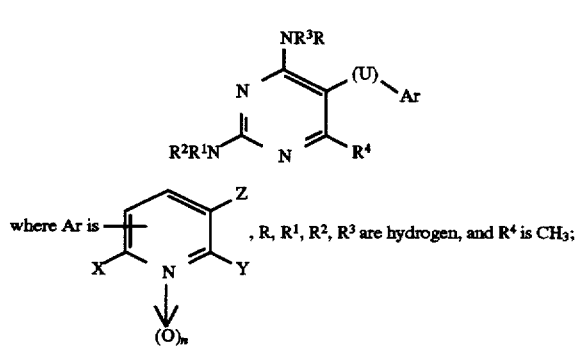

where Ar is [pyridinyl structure with substituents X, Y, Z and N→(O)ₙ], R, R¹, R², R³ are hydrogen, and R⁴ is CH₃;

| Cmpd No. | U | pyridinyl[(a)] | n | X | Y | Z |
|---|---|---|---|---|---|---|
| 198 | —CH=CHC(CH₃)₂— | 4 | 0 | t-Bu | t-Bu | H |
| 199 | —CH=CHC(CH₃)₂— | 4 | 1 | t-Bu | t-Bu | H |

TABLE 1-continued

Pesticidal 5-[ω-(Substituted aryl)-alkenylene and alkynylene]-2,4-diaminopyrimidines

| | | | | | | |
|---|---|---|---|---|---|---|
| 200 | —CH=CHC(CH₃)₂— | 4 | 0 | H | H | H |
| 201 | —C≡CC(CH₃)₂— | 4 | 0 | t-Bu | t-Bu | H |
| 202 | —C≡CC(CH₃)₂— | 4 | 1 | t-Bu | t-Bu | H |
| 203 | —C≡CC(CH₃)₂— | 4 | 0 | H | H | H |
| 204 | —CH=CHC(CH₃)₂— | 2 | 0 | —[a] | H | CF₃ |
| 205 | —CH=CHC(CH₃)₂— | 2 | 1 | — | H | CF₃ |
| 206 | —CH=CHC(CH₃)₂— | 2 | 0 | — | H | Cl |
| 207 | —CH=CHC(CH₃)₂— | 2 | 1 | — | H | Cl |
| 208 | —CH=CHC(CH₃)₂— | 2 | 0 | — | H | H |
| 209 | —C≡CC(CH₃)₂— | 3 | 0 | H | CF₃ | H |
| 210 | —C≡CC(CH₃)₂— | 3 | 1 | H | CF₃ | H |
| 211 | —C≡CC(CH₃)₂— | 3 | 0 | H | Cl | H |
| 212 | —C≡CC(CH₃)₂— | 3 | 1 | H | Cl | H |
| 213 | —C≡CC(CH₃)₂— | 3 | 0 | H | H | H |
| 214 | —CH=CHC(CH₃)₂— | 3 | 0 | H | CF₃ | H |
| 215 | —CH=CHC(CH₃)₂— | 3 | 1 | H | CF₃ | H |
| 216 | —CH=CHC(CH₃)₂— | 3 | 0 | H | Cl | H |
| 217 | —CH=CHC(CH₃)₂— | 3 | 1 | H | Cl | H |
| 218 | —CH=CHC(CH₃)₂— | 3 | 1 | H | H | H |
| 219 | —C≡CC(CH₃)₂— | 2 | 0 | —[a] | H | CF₃ |
| 220 | —C≡CC(CH₃)₂— | 2 | 1 | — | H | CF₃ |
| 221 | —C≡CC(CH₃)₂— | 2 | 0 | — | H | Cl |
| 222 | —C≡CC(CH₃)₂— | 2 | 1 | — | H | Cl |
| 223 | —C≡CC(CH₃)₂— | 2 | 1 | — | H | H |

[a] position of ring attachment

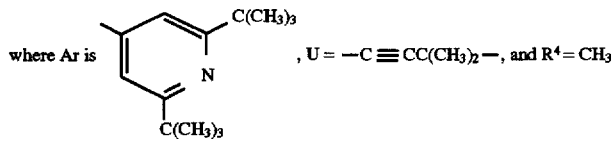

where Ar is (structure), U = —C≡CC(CH₃)₂—, and R⁴ = CH₃

| Cmpd No. | R¹ | R² | R³ | R |
|---|---|---|---|---|
| 224 | C(O)(CH₂)₃CN | H | C(O)(CH₂)₃CN | H |
| 225 | C(O)CH₂OCH₃ | H | C(O)CH₂OCH₃ | H |
| 226 | C(O)CH₃ | H | C(O)CH₃ | H |

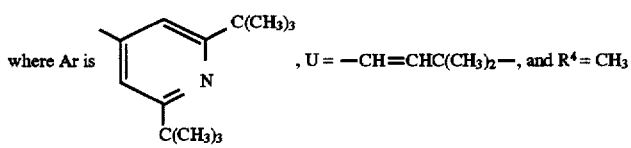

where Ar is (structure), U = —CH=CHC(CH₃)₂—, and R⁴ = CH₃

| 227 | C(O)(CH₂)₃CN | H | C(O)(CH₂)₃CN | H |
| 228 | C(O)CH₂OCH₃ | H | C(O)CH₂OCH₃ | H |
| 229 | C(O)CH₃ | H | C(O)CH₃ | H |

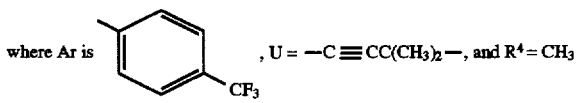

where Ar is (structure), U = —C≡CC(CH₃)₂—, and R⁴ = CH₃

| 230 | CH₃ | H | H | H |
| 231 | CH₃ | H | CH₃ | H |
| 232 | H | H | CH₃ | H |
| 233 | C₂H₅ | H | H | H |
| 234 | C₂H₅ | H | C₂H₅ | H |
| 235 | H | H | C₂H₅ | H |

TABLE 1-continued
Pesticidal 5-[ω-(Substituted aryl)-alkenylene and alkynylene]-2,4-diaminopyrimidines
| # | | | | |
|---|---|---|---|---|
| 236 | H | 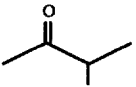 | CH₃ | H |
| 237 | CH₃ | H | H | 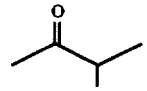 |
| 238 | H | 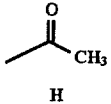 | C₂H₅ | H |
| 239 | C₂H₅ | H | H | 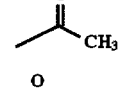 |
| 240 | H | 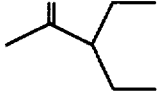 | H | 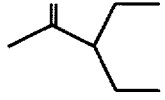 |
| 241 | 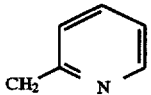 | H | H | H |
| 242 | H | H | 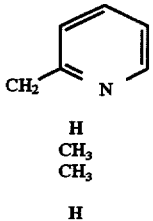 | H |
| 243 | CH₃ | CH₃ | H | H |
| 244 | H | H | CH₃ | CH₃ |
| 245 | CH₃ | CH₃ | CH₃ | CH₃ |
| 246 | H | 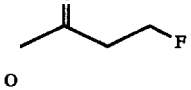 | H | 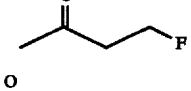 |
| 247 | H | 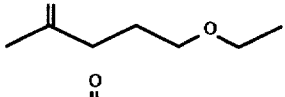 | H | 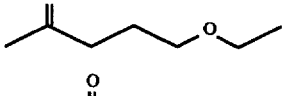 |
| 248 | H | 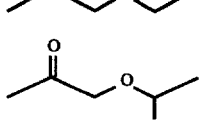 | H | 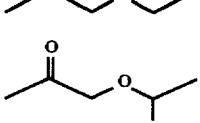 |
| 249 | H |  | H |  |
| 250 | H | 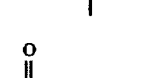 | H |  |
| 251 | H | 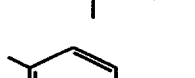 | H |  |
where Ar is 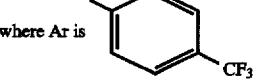, U= —CH=CHC(CH₃)₂—, R⁴=CH₃
| 252 | CH₃ | H | H | H |
| 253 | CH₃ | H | CH₃ | H |
| 254 | H | H | CH₃ | H |
| 255 | C₂H₅ | H | H | H |

TABLE 1-continued
Pesticidal 5-[ω-(Substituted aryl)-alkenylene and alkynylene]-2,4-diaminopyrimidines
| | | | | |
|---|---|---|---|---|
| 256 | C₂H₅ | H | C₂H₅ | H |
| 257 | H | H | C₂H₅ | H |
| 258 | H | 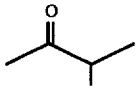 | CH₃ | H |
| 259 | CH₃ | H | H | 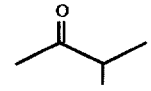 |
| 260 | H |  | C₂H₅ | H |
| 261 | C₂H₅ | H | H | 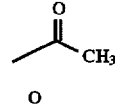 |
| 262 | H | 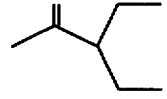 | H | 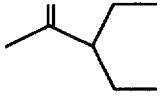 |
| 263 | 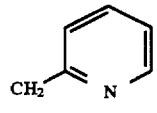 | H | H | H |
| 264 | H | H | 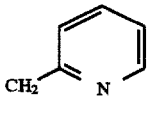 | H |
| 265 | CH₃ | CH₃ | H | H |
| 266 | H | H | CH₃ | CH₃ |
| 267 | CH₃ | CH₃ | CH₃ | CH₃ |
| 268 | H | 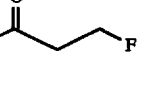 | H | 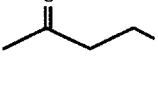 |
| 269 | H | 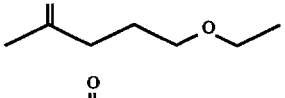 | H | 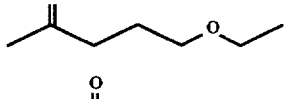 |
| 270 | H | 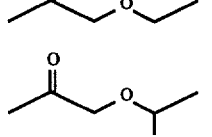 | H | 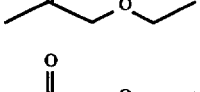 |
| 271 | H |  | H | 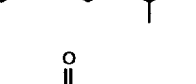 |
| 272 | H | 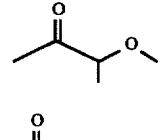 | H | 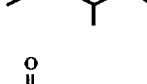 |
| 273 | H | 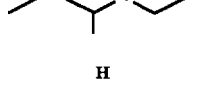 | H | 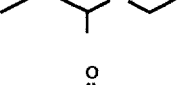 |
| 274 | C₄H₉ | H | 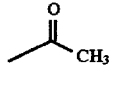 | 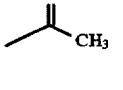 |

TABLE 1-continued

Pesticidal 5-[ω-(Substituted aryl)-alkenylene and alkynylene]-2,4-diaminopyrimidines

| 275 | H | 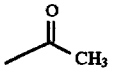 | H | 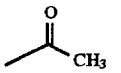 | where Ar is 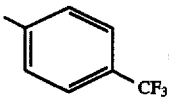 , U = —C≡CC(CH₃)₂—, and R⁴ = CH₃

| 276 | 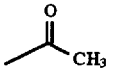 | 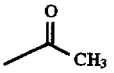 | 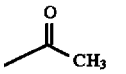 | 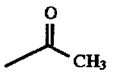 | where Ar is 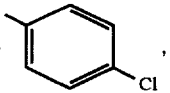 , U is —C≡CC(CH₃)₂—, and R⁴ = CH₃

| 277 | H | 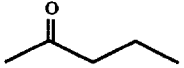 | H | 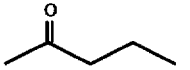 |

Insecticide and Acaricide Formulations

In the normal use of the pesticidal pyrimidines of the present invention, they usually will not be employed free from admixture or dilution, but ordinarily will be used in a suitable formulated composition compatible with the method of application and comprising an insecticidally or acaricidally effective amount of the pyrimidine. The pyrimidines of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present pyrimidines may be applied, for example, as sprays, dusts, or granules to the area where pest control is desired, the type of application varying of course with the pest and the environment. Thus, the pyrimidines of this invention may be formulated as granules of large particle size, as powdery dusts, as wettable powders, as emulsifiable concentrates, as solutions, and the like. It will be understood that the pesticides themselves may be present as essentially pure compounds, or as mixtures of these pyrimidine compounds.

Granules may comprise porous or nonporous particles, such as attapulgite clay or sand, for example, which serve as carriers for the pyrimidines. The granule particles are relatively large, a diameter of about 400-2500 microns typically. The particles are either impregnated with the pyrimidine from solution or coated with the pyrimidine, adhesive sometimes being employed. Granules generally contain 0.05-10%, preferably 0.5-5%, active ingredient as the pesticidally effective amount.

Dusts are admixtures of the pyrimidines with finely divided solids such as talc, attapulgite clay, kieselguhr, pyrophyllite, chalk, diatomaceous earths, calcium phosphates, calcium and magnesium carbonates, sulfur, flours, and other organic and inorganic solids which acts as carriers for the insecticide. These finely divided solids have an average particle size of less than about 50 microns. A typical dust formulation useful for controlling insects contains 1 part of 2,4-diamino-6-methyl-5-[3-(4-chlorophenyl)-3-methyl-1-butenyl]pyrimidine and 99 parts of talc.

The pyrimidines of the present invention may be made into liquid concentrates by dissolution or emulsification in suitable liquids and into solid concentrates by admixture with talc, clays, and other known solid carriers used in the pesticide art. The liquid concentrates and wettable powders are compositions containing, respectively, as a pesticidally effective amount, about 5-50%, and 10-50% pyrimidine, the balance comprising inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

By way of illustration, Compound 21 was formulated as a 10% wettable powder (10% WP) as follows:

| COMPONENT | AMOUNT (wt/wt) |
|---|---|
| Compound 21 | 10.1% |
| Wetting Agent | 5.0% |
| Dispersing Agent | 3.5% |
| Wetting/Dispersing Agent | 0.9% |
| Diluent | 80.2% |

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the pyrimidines with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts, including fatty methyl taurides; alkylaryl polyether alcohols; sulfates of higher alcohols; polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 5–10% by weight of the insecticidal composition.

Other useful formulations include simple solutions of the active ingredient in a solvent in which it is completely soluble at the desired concentrations, such as acetone or other organic solvents.

As shown in the biological test methods below, the compounds of the present invention were tested in the laboratory as dimethylsulfoxide solutions incorporated into an artificial insect or acarid diet or as aqueous acetone or methanol solutions containing a small amount of octylphenoxy-polyethoxyethanol surfactant for use as foliar sprays. A pesticidally effective amount of pyrimidine in a composition diluted for laboratory application is normally in the range of about 0.00001% to about 0.005% by weight, (i.e. 1 part to 50 parts per million) preferably 0.00001 to 0.003%. Many variations of spraying and dusting compositions known in the art may be used by substituting the pyrimidine of this invention into compositions known or apparent in the art.

The pesticidal compositions of this invention may be formulated with other active ingredients, including other insecticides, nematicides, other acadcides, fungicides, plant growth regulators, fertilizers, etc.

In using the compositions to control insects or acarids, it is only necessary that a pesticidally effective amount of pyrimidine be applied to the locus where control is desired. Such locus may, e.g., be the insects or acarids themselves, plants upon which they feed, or their habitat. When the locus is the soil, e.g., soil in which agricultural crops are or will be planted, the active compound may be applied to and optionally incorporated into the soil. For most applications, a pesticidally effective amount will be about 10 to 1000 g per hectare, preferably 10 g to 500 g.

Biological Data

The substituted 2,4-diaminopyrimidines of the present invention were first incorporated into an artificial diet for evaluation of insecticidal activity against the tobacco budworm (*Heliothis virescens* [Fabdcius]).

Stock solutions of test chemical in dimethylsulfoxide were prepared for each rate of application. The rates of application, expressed as the negative log of the molar concentration, and the corresponding concentrations of the stock solution prepared for each rate are shown below:

| Stock Solution | Rate of Application |
| --- | --- |
| 50 micromolar | 4 |
| 5 | 5 |
| 0.5 | 6 |
| 0.05 | 7 |
| 0.005 | 8 |

One hundred microliters of each of the stock solutions was manually stirred into 50 mL of a molten (65°–70° C.) wheat germ-based artificial diet. The 50 mL of molten diet containing the test chemical was poured evenly into twenty wells in the outer four rows of a twenty-five well, five row plastic tray. Each well in the tray was about 1 cm in depth, with an opening of 3 cm by 4 cm at the lip. Molten diet containing only dimethylsulfoxide at the levels used in the test chemical-treated diet was poured into the five wells in the third row of the tray. Each tray therefore contained one test chemical at a single rate of application, together with an untreated control.

Single second instar tobacco budworm larvae were placed in each well. The larvae were selected at a stage of growth at which they uniformly weigh about 5 mg each. Upon completion of infestation, a sheet of clear plastic was heat-sealed over the top of the tray using a common household flat iron. The trays were held at 25° C. at 60% relative humidity for five days in a growth chamber. Lighting was set at 14 hours of light and 10 hours of darkness.

After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pI_{50}$) was determined by linear regression, when possible, for each test chemical. Where possible, the negative log of the concentration of the test chemical that provided 50% mortality ($pLC_{50}$) was also determined. These data are presented in Table 2. Table 3, which is supplemental to Table 2, discloses the corresponding results for additional compounds, using the same procedures as in Table 2, where the application rate is 5 (as defined in Table 2).

As shown in Tables 2 and 3, the compounds of the present invention inhibited the growth of tobacco budworm. Included amongst the more efficacious, and thus preferred, compounds are, for example, Compounds 22, 43, 68, 80, 111, 117, 120, 126, 142 and 165 of Table 1.

Foliar Tests

Certain substituted-2,4-diaminopyrimidine derivatives with high $pI_{50}$ values from the diet test were also tested for insecticidal activity in foliar evaluations against the tobacco budworm (TBW), beet armyworm (BAW) (*Spodoptera exigua* Hubner]), and the cabbage looper (CL) (*Trichoplusia ni* [Hubner]).

In these tests against the tobacco budworm and the beet armyworm, nine-day-old chick pea plants (*Cicer arietinum*) were sprayed at 20 psi to runoff on both upper and lower leaf surfaces with solutions of test chemical to provide application rates as high as 1000 ppm of test chemical. The solvent used to prepare the solutions of test chemical was 10% acetone or methanol (v/v) and 0.1% of the surfactant octylphenoxypolyethoxyethanol in distilled water. Four replicates, each containing four chick pea plants, for each rate of application of test chemical were sprayed. The treated plants were transferred to a hood where they were kept until the spray had dried.

The four chick pea plants in each replicate treated with test chemical as described above were removed from their pots by cutting the stems just above the soil line. The excised leaves and stems from the four plants in each replicate were placed in individual 8-ounce paper cups, which contained a moistened filter paper. Five second-instar (4–5 days old) tobacco budworms or beet armyworms were counted into each cup, taking care not to cause injury. An opaque plastic lid was placed on each cup, which was then held in a growth chamber for a 96 hour exposure period at 25° C. and 50% relative humidity. At the end of the 96 hour exposure period the cups were opened, and the numbers of dead and live insects were counted. Moribund larvae which were disoriented or unable to crawl normally were counted as dead. Using the insect counts, the efficacy of the test chemical i.e., the percent mortality, was expressed as percent control in Table 4 below. The condition of the test plants was also observed for phytotoxicity and for reduction of feeding damage as compared to an untreated control. Table 5, which is supplemental to Table 4, discloses the corresponding results for additional compounds, using the same procedures as in Table 4, where the application rate is 3 (ppm).

Foliar tests with cabbage looper were conducted in the same manner as described above, the difference being that pinto bean plants (*Phaseolus vulgaris*) were used.

Of the compounds evaluated on foliage for insecticidal activity, the more active, and thus preferred ones include Compounds 7, 8, 21, 68, 72, 74, 84, 88, 90, 111, 130 and 137 of Table 1.

In a further embodiment of this invention, it has been found that in addition to the excellent activity of the compounds of this invention against the Order Lepidoptera, as shown in Tables 2 to 5 above, these compounds have also been determined to be active against Orders Acarina and Coleoptera. Data showing their effectiveness as acarides, particularly as miticides, as well as broader insecticidal activity, are set forth in Table 6 where there is provided the percent control of selected compounds against twospotted spider mite (TSM-S) (*Tetranychus urticae* Koch) and Mexican bean beetle (MBB) (*Epilachna varivestis* Mulsant), respectively, at an application rate of 10 (ppm).

The foliar test to show insecticidal activity against Mexican bean beetle is conducted in the same manner as the foliar test against cabbage looper (Tables 4 and 5 above). The foliar test to show acaricidal activity against twospotted spider mite is conducted as follows:

Two seven-day-old pinto bean plants for each rate of application are each infested with 50 to 100 adult female twospotted spider mites about one hour prior to spraying with the candidate acaricide. Using test solutions of the candidate acaricide, prepared as described for foliar testing, (above) the test plants am sprayed with test solution at 15 psi to runoff on both upper and lower leaf surfaces. The treated test plants are then held in a growth chamber for an exposure period of 96 hours at 25° C. and 50% relative humidity. At the end of the exposure period each leaf from the test plant is removed from the plant and examined under a microscope, and the number of dead and live mites are recorded. Percent control is assessed in the same manner as described for foliar testing.

The effectiveness of other compounds of this invention against the Orders Acarina and Coleoptera may be routinely determined by conventional testing techniques, employing the above-described diet and/or foliar testing in order to select application rates and activity of the rate of magnitude desired, particularly ones comparable to those shown in Tables 2 to 5 above.

Summary of Biological Data: Preferred Compounds

Among the more preferred compounds of Table 1, as shown by their activity in Tables 2 to 5, are Compounds 7, 8, 21, 22, 43, 68, 72, 74, 80, 84, 88, 90, 111, 117, 120, 126, 130, 137, 142, and 165.

In addition, there are also preferred, because of their pesticidal effectiveness, Compounds 66, 269, 275, 276, and 277.

Of the above compounds, most preferred are Compounds 21, 43, 68, 84, and 165.

These compounds are preferred not only because of their high degree of pesticidal activity, especially against Lepidoptera and Coleoptera, but also because of their ability to maintain this effectiveness at low application rates.

TABLE 2

Pesticidal Activity of 5-[ω-(Substituted aryl)-alkenylene and alkynylene]-2,4-diaminopyrimidines Incorporated into the Diet of Tobacco Budworm

| Cmpd. No. | Rate of Application[1] | Percent Growth Inhibition[2,3] | $pI_{50}$[4] | Percent Mortality[5] | $pLC_{50}$[6] |
|---|---|---|---|---|---|
| 7 | 8 | 1 | 7.1 | 0 | 5.4 |
|   | 7 | 75 |   | 0 |   |
|   | 6 | 97 |   | 35 |   |
|   | 5 | 99 |   | 65 |   |
|   | 4 | 100 |   | 90 |   |
|   | 8 | 18 | 7.5 | 0 | 5.2 |
|   | 7 | 81 |   | 20 |   |
|   | 6 | 97 |   | 40 |   |
|   | 5 | 99 |   | 60 |   |
|   | 4 | 100 |   | 90 |   |
|   | 7.5 | 9 | 7.3 | 0 | 6.6 |
|   | 7 | 88 |   | 35 |   |
|   | 6 | 100 |   | 80 |   |
|   | 5 | 100 |   | 85 |   |
|   | 4 | 100 |   | 90 |   |
|   | 7 | 86 | >7.0 | 15 | 6.0 |
|   | 6.5 | 96 |   | 40 |   |
|   | 6 | 99 |   | 45 |   |
|   | 5 | 100 |   | 85 |   |
|   | 4 | 100 |   | 85 |   |
|   | 8 | 7 | 7.5 | 0 | 6.7. |
|   | 7 | 87 |   | 30 |   |
|   | 6 | 100 |   | 85 |   |
|   | 5 | 100 |   | 90 |   |
| 21 | 7 | 94 | >7.0 | 40 | 6.8 |
|   | 6 | 99 |   | 80 |   |
|   | 5 | 100 |   | 90 |   |
|   | 4 | 100 |   | 95 |   |
|   | 8 | 14 | 7.3 | 0 | 6.9 |
|   | 7 | 74 |   | 35 |   |
|   | 6 | 100 |   | 95 |   |
|   | 5 | 100 |   | 80 |   |
| 30 | 6 | 2 | 4.5 | 0 | — |
|   | 5 | 25 |   | 0 |   |
|   | 4 | 72 |   | 0 |   |
| 32 | 6 | 1 | 5.3 | 0 | — |
|   | 5 | 75 |   | 0 |   |
|   | 4 | 93 |   | 0 |   |
| 33 | 5 | 81 | >5.0 | 15 | <4.0 |
|   | 4 | 90 |   | 25 |   |
|   | 6 | 10 | 5.2 | 0 | — |
|   | 5 | 72 |   | 0 |   |
|   | 4 | 93 |   | 20 |   |
| 34 | 7 | −3 | 5.8 | 0 | 4.1 |
|   | 6 | 36 |   | 0 |   |
|   | 5 | 90 |   | 5 |   |
|   | 4 | 99 |   | 55 |   |
| 35 | 7 | 0 | 5.5 | 0 | — |
|   | 6 | 16 |   | 0 |   |
|   | 5 | 82 |   | 10 |   |
|   | 4 | 94 |   | 20 |   |
| 36 | 5 | 79 | >5.0 | 20 | 4.0 |
|   | 4 | 93 |   | 50 |   |
|   | 6 | 4 | 5.1 | 0 | — |
|   | 5 | 63 |   | 0 |   |
|   | 4 | 93 |   | 15 |   |
| 37 | 6 | 4 | 5.1 | 0 | — |
|   | 5 | 62 |   | 5 |   |
|   | 4 | 94 |   | 20 |   |
| 38 | 6 | 12 | 5.2 | 0 | — |
|   | 5 | 71 |   | 0 |   |
|   | 4 | 92 |   | 0 |   |
| 39 | 7 | 25 | 6.1 | 0 | — |
|   | 6 | 50 |   | 0 |   |
|   | 5 | 88 |   | 0 |   |
|   | 4 | 96 |   | 5 |   |
| 42 | 6 | 13 | 5.4 | 15 | — |
|   | 5 | 80 |   | 20 |   |
|   | 4 | 89 |   | 0 |   |
| 43 | 8 | 5 | 7.5 | 0 | 6.3 |
|   | 7 | 87 |   | 25 |   |

TABLE 2-continued

Pesticidal Activity of 5-[ω-(Substituted aryl)-alkenylene and alkynylene]-2,4-diaminopyrimidines Incorporated into the Diet of Tobacco Budworm

| Cmpd. No. | Rate of Application[1] | Percent Growth Inhibition[2,3] | $pI_{50}$[4] | Percent Mortality[5] | $pLC_{50}$[6] |
|---|---|---|---|---|---|
|    | 6 | 97 |     | 70  |     |
|    | 5 | 97 |     | 85  |     |
|    | 4 | 98 |     | 100 |     |
| 44 | 5 | 3  | <4.0 | 0  | —   |
|    | 4 | 35 |     | 0   |     |
| 63 | 5 | 8  | 4.4 | 0   | —   |
|    | 4 | 75 |     | 0   |     |
| 64 | 5 | 19 | 4.5 | 0   | —   |
|    | 4 | 78 |     | 0   |     |
| 65 | 7 | 31 | 6.5 | 0   | 4.1 |
|    | 6 | 77 |     | 0   |     |
|    | 5 | 92 |     | 10  |     |
|    | 4 | 99 |     | 55  |     |
| 66 | 8 | 8  | 7.5 | 0   | 6.6 |
|    | 7 | 88 |     | 25  |     |
|    | 6 | 99 |     | 80  |     |
|    | 5 | 99 |     | 80  |     |
|    | 4 | 100 |    | 90  |     |
|    | 8 | 2  | 7.4 | 0   | 6.5 |
|    | 7 | 83 |     | 15  |     |
|    | 6 | 98 |     | 85  |     |
|    | 5 | 98 |     | 95  |     |

FOOTNOTES

[1] The rate of application is expressed as the negative log of the molar concentration of the test compound in the diet.
[2] Percent growth inhibition is derived from the total weight of the insects (IW) at each rate of application in the test relative to the total weight of insects in an untreated control,
% Gr. Inh. = [IW (control) − IW (test)/IW (control)] × 100
[3] A minus % growth inhibition indicates that the insects weighed more at the termination of the test than those in the untreated control.
[4] $pI_{50}$ is the negative log of the concentration of the test chemical that provides 50% growth inhibition in the test insects.
[5] Percent mortality is derived from the number of dead insects (TD) relative to the total number of insects (TI) used in the test,
% Mortality = $\frac{TD}{TI}$ × 100
[6] $pLC_{50}$ is the negative log of the concentration of the test chemical that provides 50% mortality of the test insects.

TABLE 3

Pesticidal Activity of 5-[ω-(Substituted aryl)-alkenylene and alkynylene]-2,4-diaminopyrimidines Incorporated into the Diet of Tobacco Budworm

| Cmpd. No. | Rate of Application[1] | Percent Growth Inhibition[2,3] | Percent Mortality[4] |
|---|---|---|---|
| 8  | 5 | 99  | 60 |
| 11 | 5 | 100 | 95 |
| 22 | 5 | 100 | 70 |
| 24 | 5 | 89  | 15 |
| 25 | 5 | 44  | 0  |
| 28 | 5 | 90  | 0  |
| 67 | 5 | 92  | 5  |
| 68 | 5 | 99  | 75 |
| 70 | 5 | 94  | 70 |
| 71 | 5 | 97  | 50 |
| 72 | 5 | 98  | 45 |
| 73 | 5 | 96  | 60 |
| 74 | 5 | 98  | 50 |
| 76 | 5 | 97  | 20 |
| 77 | 5 | 100 | 85 |
| 78 | 5 | 99  | 70 |
| 80 | 5 | 98  | 55 |
| 82 | 5 | 100 | 75 |
| 83 | 5 | 100 | 85 |
| 84 | 5 | 100 | 95 |
| 86 | 5 | 89  | 15 |
| 87 | 5 | 99  | 65 |
| 88 | 5 | 99  | 55 |
| 89 | 5 | 96  | 20 |
| 90 | 5 | 96  | 40 |
| 92 | 5 | 96  | 20 |
| 93 | 5 | 92  | 10 |
| 94 | 5 | 99  | 60 |
| 95 | 5 | 96  | 20 |
| 96 | 5 | 93  | 20 |
| 98 | 5 | 97  | 25 |
| 99 | 5 | 96  | 10 |
| 100 | 5 | 97 | 20 |
| 104 | 5 | 100 | 80 |
| 105 | 5 | 97 | 45 |
| 106 | 5 | 91 | 0 |
| 107 | 5 | 5 | 0 |
| 111 | 5 | 100 | 85 |
| 117 | 5 | 98 | 55 |
| 120 | 5 | 100 | 90 |
| 126 | 5 | 100 | 100 |
| 129 | 5 | 98 | 55 |
| 130 | 5 | 100 | 90 |
| 131 | 5 | 99 | 75 |
| 132 | 5 | 100 | 90 |
| 133 | 5 | 95 | 10 |
| 134 | 5 | 95 | 10 |
| 135 | 5 | 96 | 5 |
| 136 | 5 | 48 | 5 |
| 137 | 5 | 98 | 45 |
| 138 | 5 | 100 | 85 |
| 139 | 5 | 96 | 30 |
| 142 | 5 | 100 | 90 |
| 154 | 5 | 97 | 65 |
| 198 | 5 | 90 | 0 |
| 201 | 5 | 77 | 5 |
| 274 | 5 | 98 | 75 |
| 275 | 5 | 98 | 85 |
| 276 | 5 | 97 | 75 |
| 277 | 5 | 99 | 75 |

FOOTNOTES

[1] The rate of application is expressed as the negative log of the molar concentration of the test compound in the diet.
[2] Percent growth inhibition is derived from the total weight of the insects (IW) at each rate of application in the test relative to the total weight of insects in an untreated control,
% Gr. Inh. = [IW (control) − IW (test)/IW (control)] × 100
[3] A minus % growth inhibition indicates that the insects weighed more at the termination of the test than those in the untreated control.
[4] Percent mortality is derived from the number of dead insects (TD) relative to the total number of insects (TI) used in the test,
% Mortality = $\frac{TD}{TI}$ × 100

TABLE 4

Pesticidal Activity of 5-[ω-(Substituted aryl)-alkenylene and alkynylene]-2,4-diaminopyrimidines Applied as Foliar Sprays

| Cmpd No. | Rate of Application (ppm) | Percent Control[1,2] | | |
|---|---|---|---|---|
|   |     | TBW | CL  | BAW |
| 7 | 300 |     |     | 100 |
|   | 100 |     |     | 100 |
|   | 30  | 100 | 100 | 95  |
|   | 10  | 100 | 100 | 80  |
|   | 3   | 95  | 100 | 22  |

TABLE 4-continued

Pesticidal Activity of 5-[ω-(Substituted aryl)-alkenylene and alkynylene]-2,4-diaminopyrimidines Applied as Foliar Sprays

| Cmpd No. | Rate of Application (ppm) | Percent Control[1,2] TBW | CL | BAW |
|---|---|---|---|---|
| | 1 | 84 | 80 | |
| | 0.3 | 6 | 15 | |
| | 30 | | 100 | 100 |
| | 10 | 20 | 100 | 95 |
| | 3 | 40 | 95 | 10 |
| | 1 | 11 | 70 | 5 |
| | 0.3 | | 15 | 0 |
| | 30 | 100 | 100 | 100 |
| | 10 | 100 | 95 | 95 |
| | 3 | 100 | 90 | 47 |
| | 1 | 100 | 95 | 20 |
| | 0.3 | 60 | 85 | 10 |
| 21 | 30 | 100 | 100 | 100 |
| | 10 | 100 | 100 | 89 |
| | 3 | 100 | 95 | 16 |
| | 1 | 95 | 95 | 5 |
| | 0.3 | 78 | 95 | 0 |
| | 30 | | | 95 |
| | 10 | 100 | 100 | 40 |
| | 3 | 100 | 100 | 15 |
| | 1 | 90 | 95 | 5 |
| | 0.3 | 89 | 80 | 0 |
| | 0.1 | 15 | 10 | |
| | 10 | 88 | | |
| | 3 | 44 | | |
| | 1 | 27 | | |
| 34 | 100 | 85 | 100 | 26 |
| | 30 | 30 | 75 | 10 |
| | 10 | 5 | 10 | 0 |
| | 3 | 0 | 0 | 0 |
| | 1 | 0 | 0 | 0 |
| 43 | 30 | | | 0 |
| | 10 | 100 | 100 | 0 |
| | 3 | 100 | 100 | 0 |
| | 1 | 94 | 90 | 0 |
| | 0.3 | 29 | 89 | 0 |
| | 0.1 | 19 | 68 | |
| 44 | 300 | 0 | 40 | 16 |
| | 100 | 0 | 5 | 0 |
| | 30 | 0 | 0 | 0 |
| | 10 | 0 | 15 | 20 |
| | 3 | 0 | 0 | 0 |
| 65 | 300 | 100 | 100 | |
| | 100 | 95 | 50 | |
| | 30 | 79 | 5 | |
| | 10 | 6 | 0 | |
| | 3 | 0 | 0 | |

FOOTNOTES
[1]TBW—tobacco budworm
CL—cabbage looper
BAW—beet armyworm
[2]Percent control is derived from the total number of dead insects (TD) plus the total number of moribund insects (TM) as compared to the total number of insects (TI) in the test:

$$\% \text{ Control} = \frac{TD + TM}{TI} \times 100$$

TABLE 5

Pesticidal Activity of 5-[ω-(Substituted aryl)-alkenylene and alkynylene]-2,4-diaminopyrimidines Applied as Foliar Sprays

| Cmpd No. | Rate of Application (ppm) | Percent Control[1,2] TBW | CL | BAW |
|---|---|---|---|---|
| 8 | 3 | 90 | 80 | — |
| 22 | 3 | 100 | 90 | 10 |
| 24 | 3 | 5 | 30 | 50 |
| 28 | 3 | 0 | 15 | 0 |
| 68 | 3 | 100 | 100 | 100 |
| 70 | 3 | 40 | 21 | 16 |
| 72 | 3 | 42 | 70 | 75 |
| 73 | 3 | 23 | — | 0 |
| 76 | 3 | 16 | 64 | 11 |
| 77 | 3 | 11 | 95 | 0 |
| 78 | 3 | 40 | 100 | 0 |
| 82 | 3 | 94 | 60 | 22 |
| 83 | 3 | — | 74 | 0 |
| 84 | 3 | 53 | 95 | 50 |
| 87 | 3 | 0 | 0 | 5 |
| 88 | 3 | 37 | 85 | 50 |
| 89 | 3 | 0 | 30 | 12 |
| 90 | 3 | 100 | 75 | 84 |
| 92 | 3 | 0 | 40 | 0 |
| 94 | 3 | 6 | 95 | 16 |
| 95 | 3 | 6 | 37 | 0 |
| 96 | 3 | 0 | 53 | 0 |
| 98 | 3 | 65 | 25 | 0 |
| 99 | 3 | 6 | 55 | 0 |
| 100 | 3 | 76 | 5 | 6 |
| 104 | 3 | 83 | 90 | 0 |
| 105 | 3 | 0 | 55 | 0 |
| 106 | 3 | 0 | 15 | 10 |
| 111 | 3 | 100 | 95 | — |
| 117 | 3 | 95 | 100 | 5 |
| 120 | 3 | 63 | 100 | 0 |
| 126 | 3 | 88 | 100 | 0 |
| 129 | 3 | 95 | 95 | 5 |
| 130 | 3 | 94 | 100 | 100 |
| 131 | 3 | 68 | 95 | 0 |
| 132 | 3 | 31 | 70 | 5 |
| 134 | 3 | 58 | 50 | 5 |
| 135 | 3 | 11 | 0 | 5 |
| 137 | 3 | 100 | 26 | 77 |
| 138 | 3 | 9 | 89 | 6 |
| 139 | 3 | 20 | 0 | 0 |
| 142 | 3 | 94 | 100 | 100 |
| 275 | 3 | 100 | 95 | 85 |
| 276 | 3 | 54 | 60 | 72 |
| 277 | 3 | 68 | 95 | 0 |

FOOTNOTES
[1]TBW—tobacco budworm
CL—cabbage looper
BAW—beet armyworm
[2]Percent control is derived from the total number of dead insects (TD) plus the total number of moribund insects (TM) as compared to the total number of insects (TI) in the test:

$$\% \text{ Control} = \frac{TD + TM}{TI} \times 100$$

TABLE 6

Insecticidal and Acaricidal Activity of 5-[ω-(Substituted aryl)-alkenylene and alkynylene]-2,4-diaminopyrimidines Applied as Foliar Sprays

| Cmpd No. | Rate of Application (ppm) | Percent Control[1,2] TSM-S | MBB |
|---|---|---|---|
| 7 | 10 | 68 | 5 |
| 8 | 10 | 15 | 0 |
| 21 | 10 | 49 | 5 |
| 22 | 10 | 76 | 0 |
| 43 | 10 | 70 | 55 |
| 66 | 10 | 43 | — |

TABLE 6-continued

Insecticidal and Acaricidal Activity of 5-[ω-(Substituted aryl)-alkenylene and alkynylene]-2,4-diaminopyrimidines Applied as Foliar Sprays

| Cmpd No. | Rate of Application (ppm) | Percent Control[1,2] | |
|---|---|---|---|
| | | TSM-S | MBB |
| 68 | 10 | 89 | — |
| 70 | 10 | 92 | 25 |
| 72 | 10 | 32 | 30 |
| 77 | 10 | 7 | — |
| 82 | 10 | 24 | — |
| 84 | 10 | 67 | 70 |
| 88 | 10 | 80 | 10 |
| 98 | 10 | 13 | 5 |
| 104 | 10 | 7 | 50 |
| 111 | 10 | 39 | 35 |
| 117 | 10 | 6 | — |
| 120 | 10 | 78 | 30 |
| 126 | 10 | 92 | 60 |
| 129 | 10 | 19 | 35 |
| 130 | 10 | 36 | 65 |
| 132 | 10 | — | 20 |

FOOTNOTES
[1]TSM-S - twospotted spider mite
MBB - Mexican bean beetle
[2]Percent control is derived from the total number of dead insects (TD) plus the total number of moribund insects (TM) as compared to the total number of insects (TI) in the test:

$$\% \text{ Control} = \frac{TD + TM}{TI} \times 100$$

In further embodiment of this invention, several of the compounds disclosed above have, themselves, been found to be novel and useful intermediates in the preparation of the 2,4-diaminopyrimidine insecticides and acaricides disclosed and claimed herein.

Included amongst these intermediate compounds are those 5-iodo compounds having the following formula:

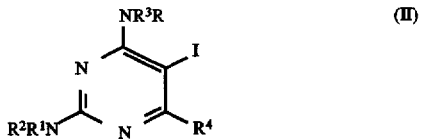

(II)

wherein
R, R$^1$, R$^2$, and R$^3$ are independently selected from hydrogen, alkyl [e.g., —CH$_3$, —C$_2$H$_5$, —C$_3$H$_7$, —CH(CH$_3$)$_2$, n-C$_8$H$_{17}$], cycloalkyl (e.g., cyclohexyl), alkoxyalkyl (e.g., —C$_3$H$_6$OC$_2$H$_5$), alkoxyalkoxyalkyl (e.g., —C$_2$H$_4$OC$_2$H$_4$OC$_2$H$_5$), or arylalkyl (e.g., phenylmethyl); or, R$^1$ and R$^2$, and R$^3$ and R, each independently, when taken together with pentylene or 3-oxapentylene, form piperidine and morpholine ring systems respectively; and R$^4$ is hydrogen or lower alkyl [e.g., —CH$_3$, —C$_2$H$_5$, —CH(CH$_3$)$_2$].

Other novel intermediates falling within the scope of this invention include those having the formula:

(III)

wherein
T is selected from —B(OH)$_2$ or —Sn(R$^5$)$_3$, where R$^5$ is lower alkyl (e.g., —CH$_3$, n-C$_4$H$_9$);
U is a C$_3$ to about C$_{12}$, preferably C$_3$—C$_8$, alkenylene [e.g. —CH=CHCH(CH$_3$)—, —CH=CHC(CH$_3$)$_2$], haloalkenylene (e.g., —CH=CHCF$_2$—, —CF=CHC(CH$_3$)$_2$—), alkoxyalkenylene [e.g., —CH=CHCH(OCH$_3$)—], 2-(1-substituted-1-cycloalkyl)alkenylene [e.g., 2-(1-substituted-1-cyclopentyl)ethenylene], 2-(substituted-oxacycloalkyl)alkenylene [e.g., 2-(4-substituted-4-tetrahydropyranyl)ethenylene], 2-[2-substituted-2-(1,3-dioxacydoalkyl)]alkenylene [e.g., 2-[2-substituted-2-(1,3-dioxolanyl)]ethenylene or 2-[2-substituted-2-(1,3-dioxanyl)]ethenylene], dialkylsilylalkenylene [e.g., —CH=CHSi(CH$_3$)$_2$—], oxoalkenylene (e.g., 3-oxo-1-propenylene) or hydroxyalkenylene [e.g., —CH=CHC(OH)CH$_3$—];

with the proviso that when U is alkenylene, it is other than 1-propenylene [e.g. —CH=CHCH$_2$—];

Ar is as defined above in Formula I, i.e., wherein
V, W, X, Y, and Z are independently selected from hydrogen, halogen, lower alkyl, lower haloalkyl, lower alkoxy, lower haloalkoxy, lower alkoxyalkyl, lower alkylsulfonyl, substituted aryl, substituted aryloxy, and hydroxy; and n is 0 or 1.

These novel intermediates, as shown in the above examples, may readily be prepared from known starting materials by conventional means. Illustration of intermediates of structure II, and their preparation, for example, include 2,4-diamino-5-iodo-6-methylpyrimidine (see Example 3). Similarly, illustrations of intermediates falling within structure III, and their preparation, include 1,1-difluoro-1-(4-chlorophenyl)-3-tributylstannyl-2-propene (see Example 4); 1-oxo-1-(4-chlorophenyl)-3-tributylstannyl-2-propene (see Example 5) as well as those of Examples 6, 11, 13, 14 and 15.

Conversion of these intermediates to the pesticide products of this invention likewise employs methods well-known to those skilled in the art; and in any event these methods are fully documented by the processes of the above examples.

In each of these methods the nature of the substituents on the final product may readily be determined by selection of the correspondingly substituted starting materials as shown in the examples above, or by introduction of such groups by means well known to those skilled in the art such as conventional halogenation or reduction reactions, or the like also shown in the above examples.

We claim:

1. A 5-iodo compound of the formula:

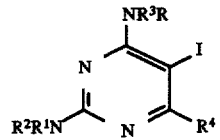

wherein
R, R$^1$, R$^2$, and R$^3$ are independently selected from hydrogen, alkyl, cycloalkyl, alkoxyalkyl, alkoxyalkoxyalkyl, and arylalkyl; or, R$^1$ and R$^2$, and R$^3$ and R, each independently, when taken together with pentylene or 3-oxapentylene, form piperidine and morpholine ring systems respectively; and, R$^4$ is hydrogen or lower alkyl.

* * * * *